United States Patent
Zhu et al.

(10) Patent No.: US 9,624,163 B2
(45) Date of Patent: Apr. 18, 2017

(54) PROCESS FOR PREPARING INTERMEDIATES USEFUL IN THE MANUFACTURE OF NEP INHIBITORS

(71) Applicant: NOVARTIS AG, Basel (CH)

(72) Inventors: Guoliang Zhu, Zhejiang (CN); Wenfa Ye, Zhejiang (CN); Hui Zheng, Zhejiang (CN); Lingfeng Qian, Zhejiang (CN); Junhui Wei, Zhejiang (CN); Lijun Yang, Zhejiang (CN); Yunguang Li, Zhejiang (CN); Lijun Luo, Zhejiang (CN)

(73) Assignees: NOVARTIS AG, Basel (CH); ZHEJIANG JIUZHOU PHARMACEUTICAL CO., LTD., Zhejiang Province (CN)

( * ) Notice: Subject to any disclaimer, the term of this patent is extended or adjusted under 35 U.S.C. 154(b) by 107 days.

(21) Appl. No.: 14/424,307

(22) PCT Filed: Sep. 2, 2013

(86) PCT No.: PCT/CN2013/082817
§ 371 (c)(1),
(2) Date: Feb. 26, 2015

(87) PCT Pub. No.: WO2014/032627
PCT Pub. Date: Mar. 6, 2014

(65) Prior Publication Data
US 2015/0210632 A1    Jul. 30, 2015

(30) Foreign Application Priority Data

Aug. 31, 2012 (CN) .......................... 2012 1 0317827
Jul. 18, 2013 (WO) ................. PCT/CN2013/079565

(51) Int. Cl.
| | | |
|---|---|---|
| C07C 213/00 | (2006.01) |
| C07C 213/02 | (2006.01) |
| C07C 269/04 | (2006.01) |
| C07C 269/06 | (2006.01) |
| C07C 29/36 | (2006.01) |
| C07C 41/30 | (2006.01) |

(52) U.S. Cl.
CPC ............ *C07C 269/04* (2013.01); *C07C 29/36* (2013.01); *C07C 41/30* (2013.01); *C07C 213/00* (2013.01); *C07C 213/02* (2013.01); *C07C 269/06* (2013.01); *C07B 2200/07* (2013.01)

(58) Field of Classification Search
CPC .... C07C 269/04; C07C 213/00; C07C 213/02
USPC .......................................................... 560/27
See application file for complete search history.

(56) References Cited

U.S. PATENT DOCUMENTS 3,462,483 A * 8/1969 Stephenson ............... B26F 1/24
                                                            514/960

FOREIGN PATENT DOCUMENTS

| WO | 9902153 | * | 1/1999 |
| WO | 9902153 | A1 | 1/1999 |
| WO | 2008031567 | A1 | 3/2008 |
| WO | 2013026773 | A1 | 2/2013 |

OTHER PUBLICATIONS

Chang, Shaohua et al., New thiazole carboxamides as potent inhibitors of Akt kinases, Bioorganic & Medicinal chemistry Letters. 2012, vol. 22 (6), pp. 1208-1212.
Barron, D.I. et al., J. Med. Chem. Nov. 30, 1968, vol. 11, Issue 6, pp. 1139-1144.

* cited by examiner

*Primary Examiner* — Kamal Saeed
*Assistant Examiner* — Janet L Coppins
(74) *Attorney, Agent, or Firm* — David R. Kurlandsky

(57) ABSTRACT

The invention relates to a new enantioselective process for producing useful intermediates for the manufacture of NEP inhibitors or prodrugs thereof, in particular NEP inhibitors comprising a γ-amino-δ-biphenyl-α-methylalkanoic acid, or acid ester, backbone.

44 Claims, No Drawings

PROCESS FOR PREPARING INTERMEDIATES USEFUL IN THE MANUFACTURE OF NEP INHIBITORS

BACKGROUND OF THE INVENTION

The invention relates to a new process for producing useful intermediates for the manufacture of NEP inhibitors or prodrugs thereof, in particular NEP inhibitors comprising a γ-amino-δ-biphenyl-α-methylalkanoic acid, or acid ester, backbone.

Endogenous atrial natriuretic peptides (ANP), also called atrial natriuretic factors (ANF) have diuretic, natriuretic and vasorelaxant functions in mammals. The natural ANF peptides are metabolically inactivated, in particular by a degrading enzyme which has been recognized to correspond to the enzyme neutral endopeptidase (NEP, EC 3.4.24.11), also responsible for e.g. the metabolic inactivation of enkephalins.

Biaryl substituted phosphonic acid derivatives are known which are useful as neutral endopeptidase (NEP) inhibitors, e.g. as inhibitors of the ANF-degrading enzyme in mammals, so as to prolong and potentiate the diuretic, natriuretic and vasodilator properties of ANF in mammals by inhibiting the degradation thereof to less active metabolites. NEP inhibitors are thus particularly useful for the treatment of conditions and disorders responsive to the inhibition of neutral endopeptidase (EC 3.4.24.11), particularly cardiovascular disorders such as hypertension, renal insufficiency including edema and salt retention, pulmonary edema and congestive heart failure.

Further neutral endopeptidase (NEP) inhibitors and their synthesis are described in U.S. Pat. No. 4,722,810, U.S. Pat. No. 5,223,516, U.S. Pat. No. 4,610,816, U.S. Pat. No. 4,929,641, South African Patent Application 84/0670, UK 69578, U.S. Pat. No. 5,217,996, EP 0306879, EP 0449523, GB 02218983, WO 92/14706, JP 06234754, EP 0361365, WO 90/09374, JP 07157459, WO 94/15908, U.S. Pat. No. 5,273,990, U.S. Pat. No. 5,294,632, U.S. Pat. No. 5,250,522, EP 0636621, WO 93/09101, EP 0511940, WO 93/10773, and U.S. Pat. No. 5,217,996. Said neutral endopeptidase (NEP) inhibitors are typically prepared by using N-acyl derivatives of biphenyl alanine as key intermediates, preferably enantiomerically pure N-acyl derivatives of biphenyl alanine such as (S)-2-acylamino-3-biphenyl propanoic acid.

For example, U.S. Pat. No. 5,217,996 describes biaryl substituted 4-amino-butyric acid amide derivatives which are useful as neutral endopeptidase (NEP) inhibitors, e.g. as inhibitors of the ANF-degrading enzyme in mammals. U.S. Pat. No. 5,217,996 discloses the preparation of N-(3-carboxyl-1-oxopropyl)-(4S)-(p-phenylphenylmethyl)-4-amino-(2R)-methyl butanoic acid ethyl ester. In the preparation of said compound N-t-butoxycarbonyl-(4R)-(p-phenylphenylmethyl)-4-amino-2-methyl-2-butenoic acid ethyl ester is hydrogenated in the presence of palladium on charcoal.

WO 2009/090251 relates to a reaction route for preparing compound N-t-butoxycarbonyl-(4S)-(p-phenylphenylmethyl)-4-amino-2-methylbutanoic acid ethyl ester, or salt thereof, wherein an alternative hydrogenation step provides improved diastereoselectivity compared to that obtained in U.S. Pat. No. 5,217,996.

Typically, synthetic methods to prepare the above mentioned biphenyl alanine derivatives in enantiomerically pure form use expensive starting materials such as non-natural D-tyrosine. Moreover, said methods require the use of trifluoromethanesulfonic anhydride, which is also expensive, to activate the phenolic hydroxyl in order to carry out the aryl coupling reaction leading to the desired biphenyl structure. One example of such a synthetic approach is described in the *J. Med. Chem.* 1995, 38, 1689-1700. The following Scheme 1 illustrates one of these methods:

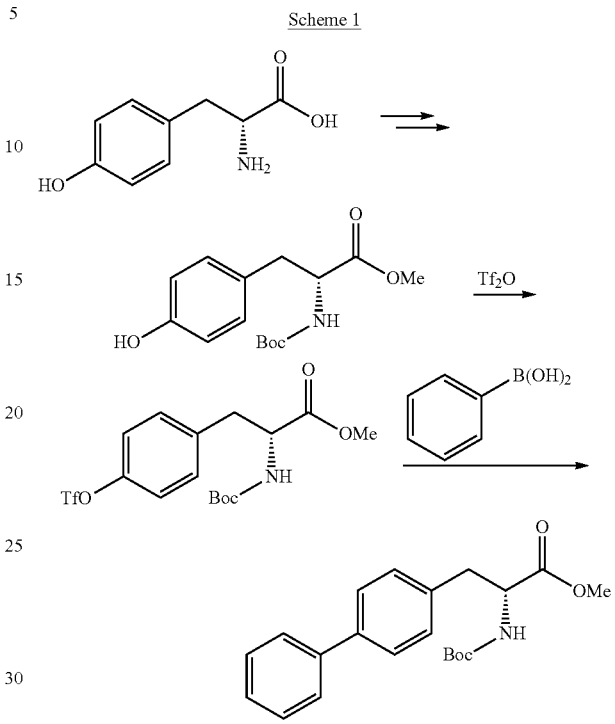

Scheme 1

Another method for preparing 2-acetylamino-3-biphenyl propanoic acid is reported in *Chemical and Pharmaceutical Bulletin* 1976, 24, 3149-3157. Said method comprises the steps i) and ii) outlined below:

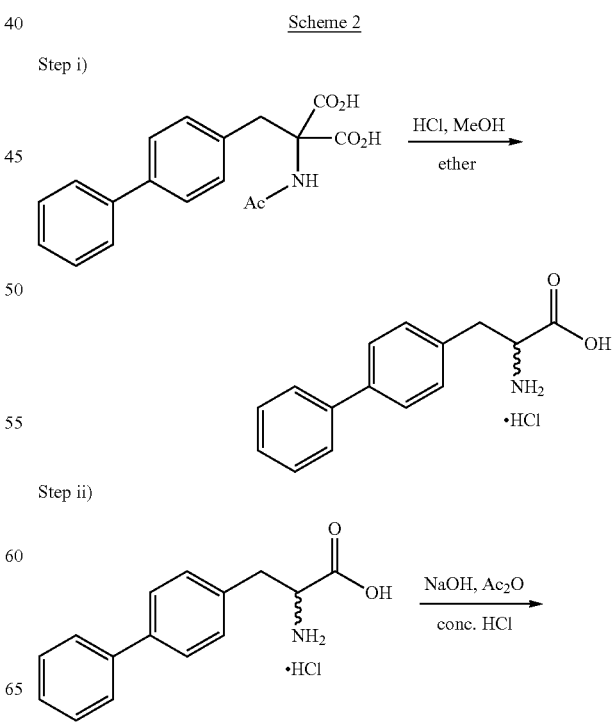

Scheme 2

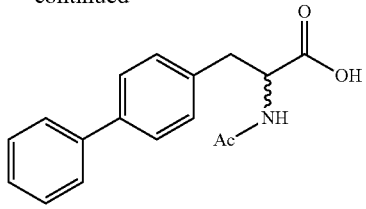

A drawback of this process is that the acetyl group is removed under the reaction conditions of the first step and thus a further chemical step is necessary in order to reintroduce it. Such an undesired acetyl removal makes thus the process unattractive. Moreover, this process does not provide means to obtain enantiomerically pure 2-acylamino-3-biphenyl propanoic acid without 10 additional resolution of the racemate, e.g. by salt formation with a chiral amine, or by enzymatic resolution.

WO 2010/081410 describes a method for obtaining an enantiomerically pure chiral compound of formula (I)

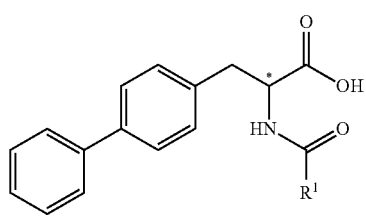

(I)

wherein said method comprises reacting a compound of formula (III)

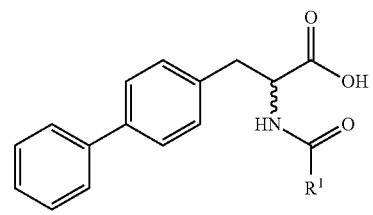

(III)

with a chiral amine of formula (V)

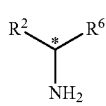

(V)

and resolving the resulting disasteromeric mixture of a compound of formula (II)

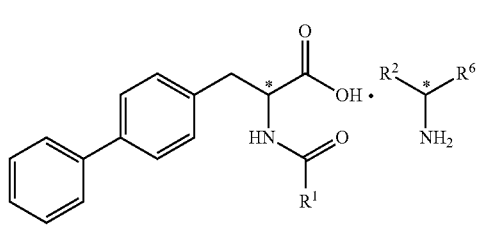

(II)

via crystallization.

However, one main disadvantage of any chiral resolution of racemates compared to a direct asymmetric synthesis of one of the enantiomers is that the yield cannot reach more than 50% at maximum. Though epimerization of the undesired enantiomer and resubmission to resolution is possible in some cases, it generally requires additional processing steps, and thereby creating an additional burden.

An alternative method for preparing an N-acylbiphenyl alanine is described in WO 2011/035569 and depicted in Scheme 3 below.

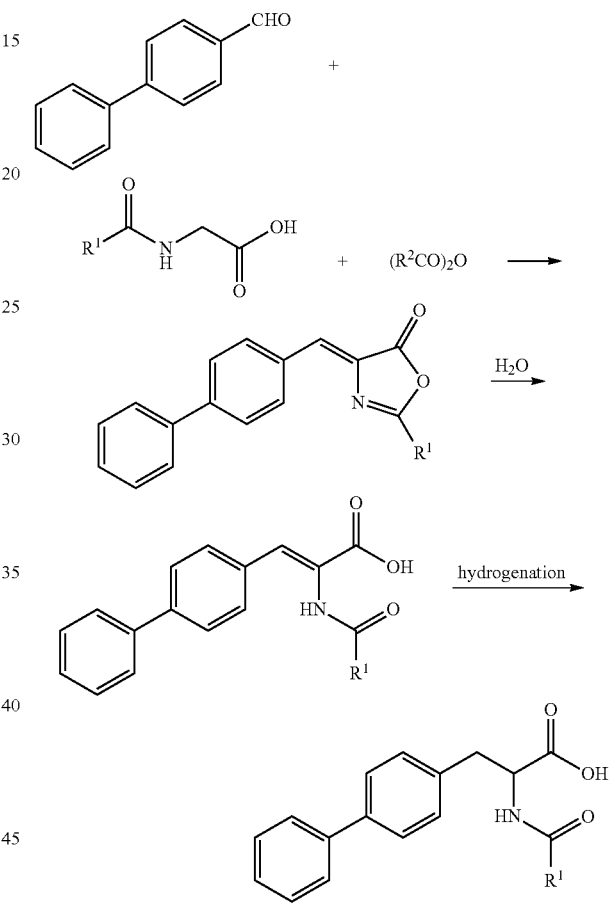

However, the synthetic process as summarized in Scheme 3 includes a catalytic hydrogenation step. The drawback to hydrogenation is that the catalyst required is almost always a precious metal such as palladium or platinum. In non-stereoselective hydrogenation reactions the metal is embedded as fine particles in activated carbon (1-5% metal loading is a common range). This material is then used for the hydrogenation reaction. Because many organic compounds may adhere to activated carbon, often times the catalyst cannot be reused for hydrogenation without extensive recycling, isolation and treatment of the precious metal. In addition, the desired product is obtained as racemic mixture under these conditions, with the associated disadvantages of non-stereoselective syntheses described above. In order to achieve stereoselective hydrogenations whilst using chiral metal catalysts, it is necessary to use an asymmetric ligand to induce selectivity. However, commonly used asymmetric ligands are often only accessible by complex synthetic routes and/or are very costly, therefore contributing significantly to the overall reaction costs. As a result, both non-stereoselective and stereoselective hydrogenation reactions on large scales are disadvantageous from an economic perspective.

Accordingly, there is a need for the development of an alternative synthesis of N-acyl derivatives of biphenyl alanine and related intermediates useful in the preparation for biaryl substituted 4-amino-butyric acid amide derivatives which act as NEP inhibitors, preferably of enantiomerically pure N-acyl derivatives of biphenyl alanine and related intermediates, which synthesis can be used on a commercial scale and which avoids the above-mentioned drawbacks of the prior art processes. Thus the object of the present invention is to provide a new process for preparing N-acyl derivatives of biphenyl alanine and related intermediates such as 3-biphenyl-2-aminopropan-1-ol and N-acyl derivatives thereof useful in the preparation of NEP inhibitors, preferably enantiomerically pure N-acyl derivatives of biphenyl alanine and related intermediates, which is suitable on a commercial scale.

SUMMARY OF THE INVENTION

The present invention relates a new process for preparing N-acyl derivatives of biphenyl alanine and related intermediates such as 3-biphenyl-2-aminopropan-1-ol and N-acyl derivatives thereof, preferably enantiomerically pure N-acyl derivatives of biphenyl alanine and related intermediates, which is suitable on a commercial scale by preparing enantiomerically pure 3-biphenyl-2-amino-propan-1-ol derivatives using a simple and low-cost method with a chiral epihalohydrin.

Enantiomerically pure 3-biphenyl-2-amino-propan-1-ol and its N-acyl derivatives are useful intermediates in the synthesis of NEP inhibitors such as biaryl substituted 4-amino-butyric acid amide derivatives. Enantiomerically pure 3-biphenyl-2-amino-propan-1-ol and its N-acyl derivatives can be either oxidized to the respective acids, i.e. N-acyl derivative of biphenyl alanine, or directly used in the synthesis of the NEP inhibitors by known processes.

The new process according to the present invention for producing a compound according to formula (1), or salt thereof, of formula (1-a) or salt thereof or of formula (1-b) or salt thereof, as defined herein, is summarized in Scheme 4, Scheme 5 and Scheme 6, respectively. The process according to the present invention is characterized by the use of an epihalohydrin, preferably a chiral epihalohydrin, in order to prepare a compound according to formula (1), or salt thereof, of formula (1-a) or salt thereof or of formula (1-b) or salt thereof, preferably of formula (1-a).

Advantages of the process of the present invention are the low number of reaction steps, the preparation of enantiomerically pure compounds, the comparably low cost and its applicability on a commercial scale.

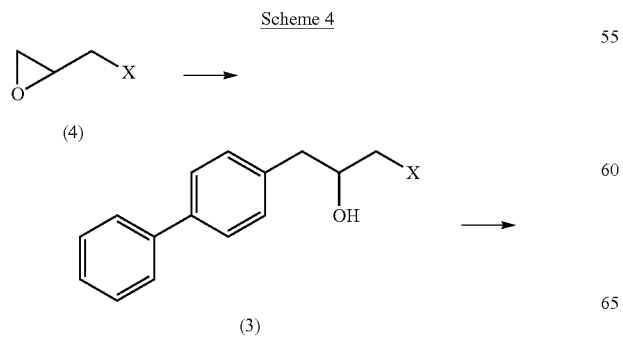

Scheme 4 relates to an embodiment of the invention wherein a compound of formula (4), as described herein, is converted into a compound of formula (1), or salt thereof, wherein X is halogen or alkoxy, R1 and R2 are independently of each other hydrogen or a nitrogen protecting group, as defined herein below, wherein at least one of R1 or R2 is a nitrogen protecting group, and R3 is an imidyl group or an azide group, as described herein below.

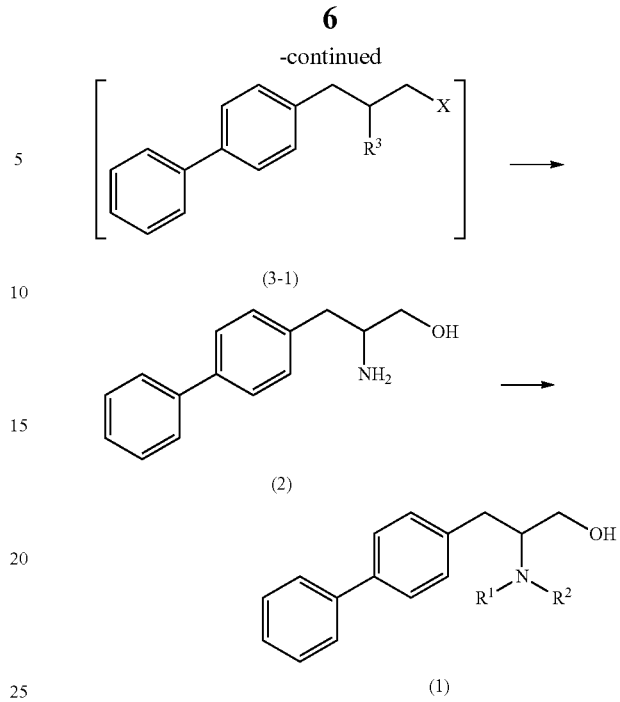

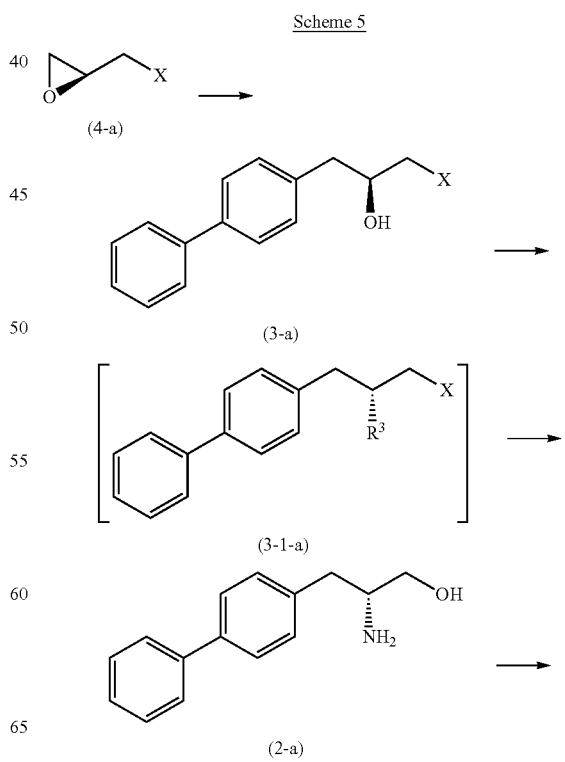

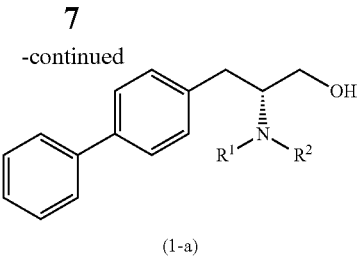

(1-a)

In one embodiment, according to Scheme 5, a compound of formula (4-a), as described herein, is converted into a compound of formula (1-a), or salt thereof, wherein X is halogen or alkoxy, R1 and R2 are independently of each other hydrogen or a nitrogen protecting group, as defined herein below, wherein at least one of R1 or R2 is a nitrogen protecting group, and R3 is an imidyl group or an azide group, as described herein below.

Scheme 6

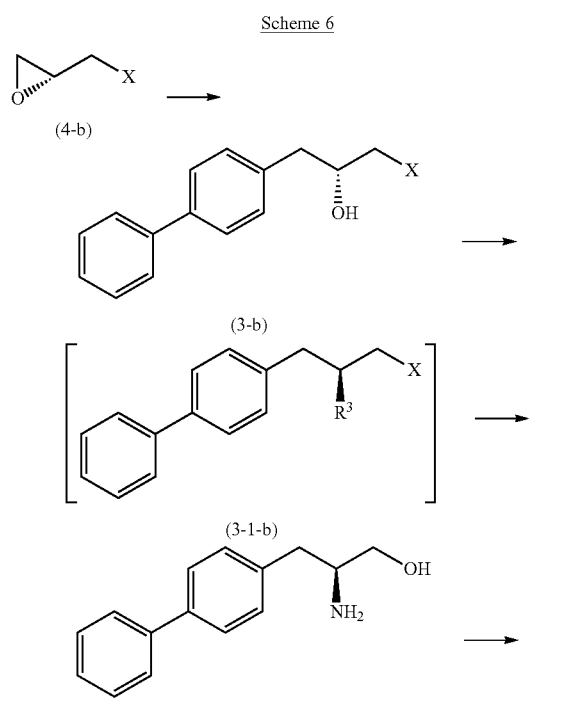

Alternatively, as depicted in Scheme 6, a compound of formula (4-b), as described herein, is converted into a compound of formula (1-b), or salt thereof, wherein X is halogen or alkoxy, R1 and R2 are independently of each other hydrogen or a nitrogen protecting group, as defined herein below, wherein at least one of R1 or R2 is a nitrogen protecting group, and R3 is an imidyl group or an azide group, as described herein below.

In the aforementioned reaction schemes, a compound of formula (4), also known as epihalohydrin, may be selected from the group consisting of epifluorohydrin, epichlorohydrin, epibromohydrin or epiiodohydrin, preferably the epihalohydrin is epichlorohydrin.

In a preferred embodiment of the invention said epihalohydrin is a chiral epihalohydrin having an (S)- or an (R)-configuration of general formula (4-a) or (4-b), respectively, preferably an (S)-configuration of formula (4-a).

In a preferred embodiment the present invention relates to a process for preparing a compound of formula (1-a) or salt thereof as shown in Scheme 5, wherein the starting compound of formula (4-a) is an (S)-epihalohydrin, selected from the group consisting of (S)-epifluorohydrin, (S)-epichlorohydrin, (S)-epibromohydrin, and (S)-epiiodohydrin. The most preferred (S)-epihalohydrin is (S)-epichlorohydrin.

DETAILED DESCRIPTION OF THE INVENTION

The following sections describe the individual process steps as laid out in Scheme 4, 5 and 6 above.

I. Preparation of a Compound of Formula (3) or Salt Thereof

This section relates to a process for the manufacture of a compound of formula (3) or a salt thereof, preferably of formula (3-a) or salt thereof as defined herein, wherein a compound of formula (4), preferably of formula (4-a) as defined herein, is reacted with a biphenylic compound to obtain a compound of formula (3) or salt thereof, preferably of formula (3-a) or salt thereof.

Accordingly, in one aspect, the subject of the present invention is a process for preparing a compound of formula (3), or a salt thereof,

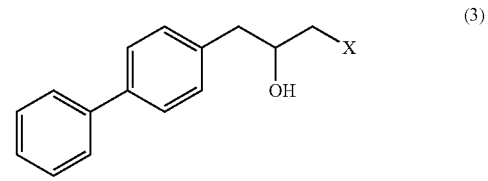

wherein X is halogen, preferably chloro, or —O—R5, wherein R5 is $C_1$-$C_6$-alkyl, preferably tert-butyl;

preferably wherein the compound of formula (3) is of formula (3-a)

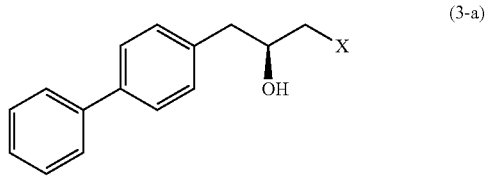

wherein X is halogen, preferably chloro, or —O—R5, wherein R5 is $C_1$-$C_6$-alkyl, preferably tert-butyl;

comprising reacting a compound of formula (4),

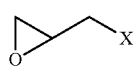
(4)

wherein X is halogen, preferably chloro, or —O—R5, wherein R5 is $C_1$-$C_6$-alkyl, preferably tert-butyl; preferably wherein the compound of formula (4) is of formula (4-a)

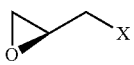
(4-a)

wherein X is halogen, preferably chloro, or —O—R5, wherein R5 is $C_1$-$C_6$-alkyl, preferably tert-butyl; with a biphenylic compound to obtain a compound of formula (3) or salt thereof, preferably formula (3-a) or salt thereof.

In another embodiment of the invention the configuration of the compound of formula (4) is a compound of formula (4-b), as described herein above and the configuration of the compound of formula (3) is a compound of formula (3-b) as described herein above.

In a preferred embodiment the biphenylic compound is activated. A suitable method for the activation is the preparation of an organometallic complex comprising a biphenyl ligand. Preferred activated biphenylic compounds include, but are not limited to biphenylmagnesium halide or di(biphenyl)magnesium (Grignard reagents). Suitable halides generally are chloride, bromide and iodide, wherein bromide is especially preferred.

Further examples for activated biphenylic compounds are biphenyllithium, biphenylcuprate (lower and higher order cuprates) and biphenylzinc.

In one embodiment of the invention the activated biphenylic compound is biphenylmagnesium bromide.

Preferably the reaction is carried out using biphenylmagnesium bromide as biphenylic compound.

Preferably, the biphenylmagnesium bromide is generated from 4-bromobiphenyl and metallic magnesium, preferably metallic magnesium powder. The magnesium might need to be activated e.g. by addition of a small amount of iodine or dibromoethane to the reaction mixture.

Those compounds can be used individually or in the presence of another metal, e.g. copper, zinc, palladium, platinum, iron, iridium or ruthenium.

Preferably the reaction is carried out in the presence of copper(I), i.e. cuprates, e.g. by addition of cuprous iodide to the reaction mixture.

Preferably the reaction is carried out using biphenylmagnesium bromide as biphenylic compound and in the presence of copper(I) ions.

Generally, 0.1 to 0.5 molar equivalents of the biphenylic compound, preferably of the biphenylmagnesium halide or di(biphenyl)magnesium, with respect to the amount of the compound of formula (4) are used. Preferably 0.2 to 0.4, more preferably 0.25, 0.3, 0.35 or 0.4 molar equivalents of the biphenylic compound, preferably of the biphenylmagnesium halide or di(biphenyl)magnesium, with respect to the amount of the compound of formula (4) are used.

In a preferred embodiment, the reaction of a compound of formula (4), preferably of formula (4-a) to provide a compound of formula (3) or salt thereof, preferably of formula (3-a) or salt thereof can be described as a regioselective epoxide ring opening using a Grignard reagent prepared from a biphenyl compound. The reaction is analogous to the Grignard addition described in *Bioorg. Med. Chem. Lett.* 2008, 18, 5238-5241, and based on the reaction as disclosed in *Heterocycles*, 1989, 29, 1825-1828, and as disclosed in Belgian Patent BE667341.

One preferred embodiment to carry out this step of the invention is depicted in the following Scheme 7.

Scheme 7

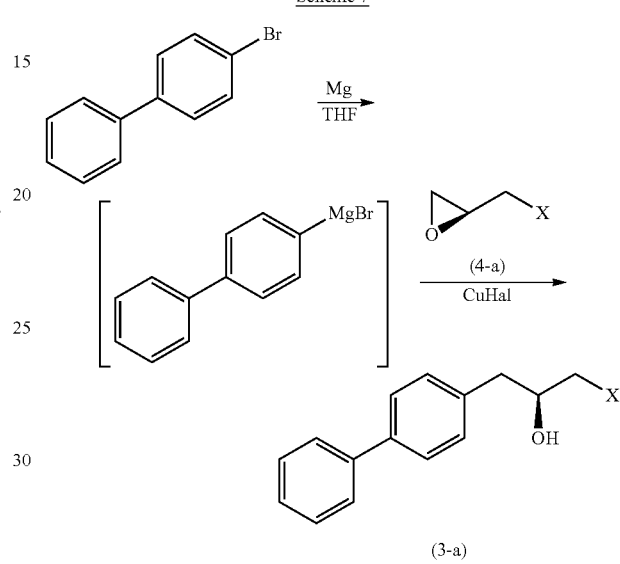

As depicted in Scheme 7, the compound of formula (3-a) is obtained by a Grignard reaction comprising reacting 4-bromobiphenyl and metallic magnesium in tetrahydrofuran and then reacting the obtained 4-biphenylmagnesium bromide with a compound of formula (4-a), wherein X is chloro or tert-butoxy, in the presence of a cuprous (I) halide, preferably cuprous iodide, as catalyst.

II. Preparation of a Compound of Formula (2) or Salt Thereof

In a further aspect, the present invention relates to a process for the manufacture of a compound of formula (2), or a salt thereof, preferably of formula (2-a) or salt thereof as defined herein, wherein a compound of formula (3) or salt thereof, preferably of formula (3-a) or salt thereof as defined herein, is reacted with a nitrogen nucleophile to obtain a compound of formula (2) or salt thereof, preferably of formula (2-a) or salt thereof.

Accordingly, in one aspect, the subject of the present invention is a process for preparing a compound of formula (2), or a salt thereof,

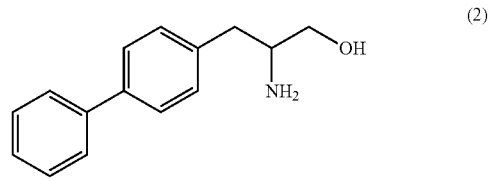 [SMILES: NC(CO)Cc1ccc(-c2ccccc2)cc1]
(2)

preferably wherein the compound of formula (2) is of formula (2-a) or salt thereof

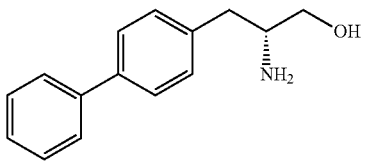

(2-a)

comprising the steps of
(a) reacting a compound of formula (3), or salt thereof

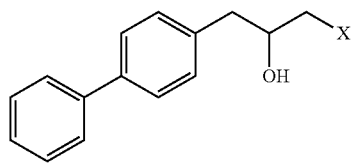

(3)

wherein X is halogen, preferably chloro, or —O—R5, wherein R5 is $C_1$-$C_6$-alkyl, preferably tert-butyl;
preferably wherein the compound of formula (3) is of formula (3-a) or salt thereof

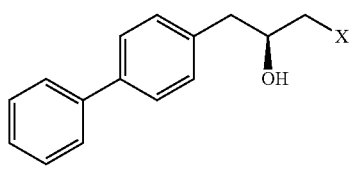

(3-a)

wherein X is halogen, preferably chloro, or —O—R5, wherein R5 is $C_1$-$C_6$-alkyl, preferably tert-butyl;
with a nitrogen nucleophile under Mitsunobu conditions, wherein said nitrogen nucleophile is an imide or an azide;
(b)
(i) conversion of the resulting imide intermediate compound of formula (3-1) or salt thereof,

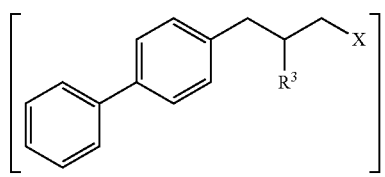

(3-1)

wherein R3 is an imide,
preferably wherein the compound of formula (3-1) is of formula (3-1-a) or salt thereof,

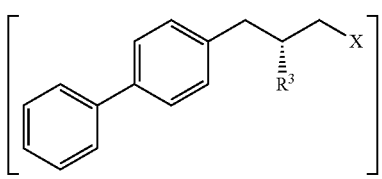

(3-1-a)

wherein R3 is imide,
by hydrolysis or by treatment with hydrazine to obtain a compound of formula (2) or salt thereof, preferably of formula (2-a) or salt thereof,
or
(ii) reduction of the resulting intermediate azide compound of formula (3-1) or salt thereof,

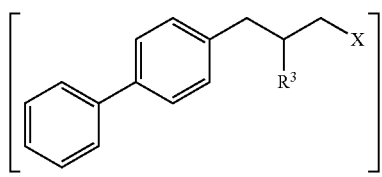

(3-1)

wherein R3 is azide,
preferably wherein the compound of formula (3-1) is of formula (3-1-a) or salt thereof,

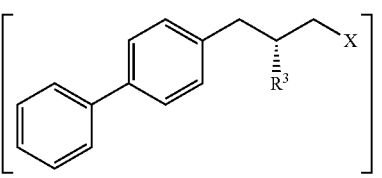

(3-1-a)

wherein R3 is azide,
to obtain a compound of formula (2) or salt thereof, preferably of formula (2-a) or salt thereof.

In one embodiment of the invention, the configuration of the compound of formula (3) is a compound of formula (3-b), as described herein above, the configuration of a compound of formula (3-1) is a compound of formula (3-1-b), as described herein and the configuration of the compound of formula (2) is a compound of formula (2-b) as described herein above.

The Mitsunobu reaction is a stereospecific substitution reaction of primary or secondary alcohols with nucleophiles. In particular this reaction is a redox condensation under mild conditions with complete Walden inversion of stereochemistry. The Mitsunobu reaction is mediated by a combination of a phosphorous(III) compound and a dialkyl azodicarboxylate.

Suitable phosphorous(III) compounds are phosphines or ylides. Phosphines suitable for the process of the present invention include, but are not limited to, triphenylphosphine, tri-n-butylphosphine, trimethylphosphine, diphenyl(2-pyridyl)phosphine, (4-dimethyl-aminophenyl)diphenylphosphine, tris-(4-dimethylaminophenyl)phosphine, 1,2-diphenylphosphinoethane and diphenyl(p-ferrocenylphenyl)phosphine. Suitable ylides for use in the present invention include, but are not limited to, (cyanomethylene)tributylphosphorane (CMBP) and (cyanomethylene)trimethylphosphorane (CMMP).

In a preferred embodiment of the invention the phosphorous(III) compound is a phosphine. In one embodiment said phosphine is selected from triphenylphosphine or tri-n-butylphosphine. Preferably said phosphine is triphenylphosphine.

The dialkyl azodicarboxylate may be selected from, but is not limited to, diethyl azodicarboxylate (DEAD), diisopropyl azodicarboxylate (DIAD), di-tert-butyl azodicarboxylate (DTBAD), 1,1'-(azodicarbonyl)dipiperidine (ADDP), 4,7- dimethyl-3,5,7-hexahydro-1,2,4,7-tetrazocin-3,8-dione (DHTD), di-p-chlorobenzyl azodicarboxylate (DCAD), N,N,N',N' tetramethyl azodicarboxamide (TMAD), N,N,N', N'-tetraisopropyl azodicarboxamide (TIPA).

In one embodiment the dialkyl azodicarboxylate is selected from diethyl azodicarboxylate (DEAD), diisopropyl azodicarboxylate (DIAD). Preferably said dialkyl azodicarboxylate is diethyl azodicarboxylate (DEAD).

The nitrogen nucleophile is an acidic compound containing an N—H group with a pka<15, preferably with a pka<11. In one embodiment the nitrogen nucleophile is an imide or an azide. Suitable imides are selected from, but are not limited to, optional substituted phthalimide, optional substituted succinimide, optional substituted naphthalimide or optional substituted maleinimide. Alternatively, the nitrogen nucleophile is an azide selected from, but not limited to, hydrazoic acid or any of its alternative sources such as trimethylsilyl azide, diphenylphosphoryl azide (DPPA) or zinc(II) azide, sodium azide, or nicotinoyl azide.

In a preferred embodiment of the invention the nitrogen nucleophile is succinimide.

In another preferred embodiment of the invention the nitrogen nucleophile is phthalimide.

A suitable solvent of the Mitsunobu reaction may be selected from tetrahydrofuran, toluene, benzene, dimethyl formamide, diethyl ether, acetonitrile, ethyl acetate, dichloromethane and 1,4-dioxane. In a preferred embodiment of the invention the solvent is toluene.

The Mitsunobu reaction is typically conducted at a temperature of between about 0° C. and about 25° C.

An intermediate imide compound of formula (3-1) or salt thereof or of formula (3-1-a) or salt thereof or of formula (3-1-b) or salt thereof can be converted to a compound of formula (2) or salt thereof, preferably of formula (2-a) or salt thereof or of formula (2-b) or salt thereof by hydrolysis, e.g. the use of an acid in the presence of water. Suitable acids are for example hydrochloric acid, acetic acid, trifluoroacetic acid, sulfuric acid or oxalic acid. Alternatively hydrolysis of the imide can be conducted by use of a base such as e.g. sodium hydroxide, sodium carbonate potassium hydroxide or potassium carbonate. Preferably, said inorganic acid is selected from hydrochloric acid and sulfuric acid; and said inorganic base is selected from sodium carbonate, potassium carbonate, sodium hydroxide, and potassium hydroxide.

In another embodiment of the invention the intermediate imide compound of formula (3-1) or salt thereof or of formula (3-1-a) or salt thereof or of formula (3-1-b) or salt thereof can be converted to a compound of formula (2) or salt thereof, preferably of formula (2-a) or salt thereof or of formula (2-b) or salt thereof by the treatment with hydrazine.

An intermediate azide compound of formula (3-1) or salt thereof or of formula (3-1-a) or salt thereof or of formula (3-1-b) or salt thereof can be converted to a compound of formula (2) or salt thereof, preferably of formula (2-a) or salt thereof or of formula (2-b) or salt thereof by reduction, e.g. with sodium borohydride, lithium aluminium hydride, triphenylphosphine and subsequent hydrolysis, $H_2$ and palladium on charcoal, stannous chloride, zinc and ammonium chloride, samarium diiodide or dichloroindium hydride.

One preferred embodiment to carry out this step of the invention is depicted in the following Scheme 8.

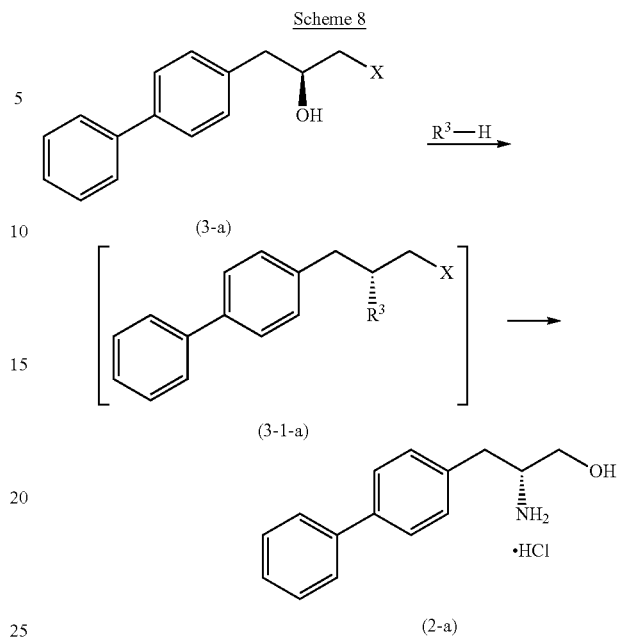

Scheme 8

As depicted in Scheme 8, in a first step a compound of formula (3-a) wherein X is chloro or tert-butoxy—preferably obtained according to the reaction as set out in Scheme 7—is reacted under Mitsunobu conditions with an imide compound of formula R3-H selected from succinimide and phthalimide in the presence of triphenyl phosphine and a dialkyl azodicarboxylate compound in an organic solvent to deliver a compound of formula (3-1-a) wherein R3 is succinimidyl or phthalimidyl. Preferably, the dialkyl azodicarboxylate compound is diethyl azodicarboxylate (DEAD). Preferably, the organic solvent is selected from toluene, ethyl acetate, tetrahydrofurane, and dichloromethane. In a second step, the obtained compound of formula (3-1-a), wherein X is chloro or tert-butoxy, and R3 is succinimidyl or phthalimidyl, is hydrolysed in the presence of an inorganic acid or an inorganic base, to obtain a compound of formula (2-a). Said inorganic acid is for example selected from hydrochloric acid and sulfuric acid; and said inorganic base is for example selected from sodium carbonate, potassium carbonate, sodium hydroxide, and potassium hydroxide. Preferably, the inorganic acid is hydrochloric acid, and the inorganic base is sodium carbonate. If the hydrolysis is carried out with the base, the obtained product is thereafter treated with hydrochloric acid in order to obtain the hydrochloride salt of the compound of formula (2-a).

III. Preparation of a Compound of Formula (1) or Salt Thereof

In a further aspect, the present invention relates to a process for the manufacture of a compound of formula (1), or a salt thereof, preferably of formula (1-a) or salt thereof as defined herein, wherein a compound of formula (2) or salt thereof, or of formula (2-a) or salt thereof as defined herein, is converted into a compound of formula (1), or salt thereof, preferably of formula (1-a) or salt thereof, wherein R1 and R2 are, independently of each other hydrogen or a nitrogen protecting group, as defined herein below, wherein at least one of R1 or R2 is a nitrogen protecting group.

Accordingly, in one aspect of the invention, a compound of formula (2), or a salt thereof,

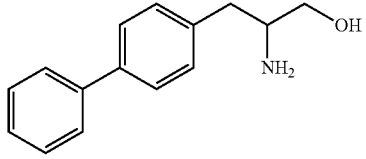
(2)

preferably wherein the compound of formula (2) is of formula (2-a) or salt thereof

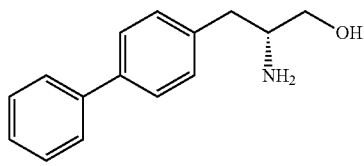
(2-a)

can be converted into a compound of formula (1), or a salt thereof,

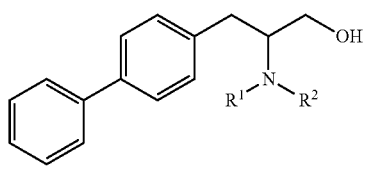
(1)

wherein R1 and R2 are, independently of each other, hydrogen or a nitrogen protecting group, wherein at least one of R1 or R2 is a nitrogen protecting group, preferably wherein the compound of formula (1) is of formula (1-a)

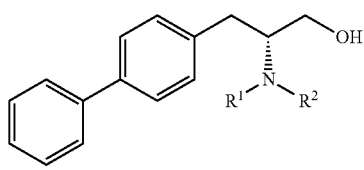
(1-a)

wherein R1 and R2 are, independently of each other, hydrogen or a nitrogen protecting group, wherein at least one of R1 or R2 is a nitrogen protecting group.

The reaction can be carried out according to standard methods of organic chemistry known in the art, in particular reference is made to conventional methods introducing nitrogen protecting group as described in J. F. W. McOmie, "Protective Groups in Organic Chemistry", Plenum Press, London and New York 1973, in T. W. Greene and P. G. M. Wuts, "Greene's Protective Groups in Organic Synthesis", fourth edition, Wiley, New York, 2007 and in Richard C. Larock, "Comprehensive Organic Transformations: A Guide to Functional Group Preparations", second edition, Wiley-VCH Verlag GmbH, 2000.

In one embodiment of the invention, the configuration of the compound of formula (2) is a compound of formula (2-b), as described herein above, and the configuration of the compound of formula (1) is a compound of formula (1-b) as described herein above.

In an particular embodiment thereof, a hydrochloride salt of the compound of formula (2-a)

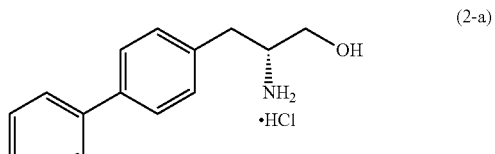
(2-a)

is converted into a compound of formula (1-a), or a salt thereof,

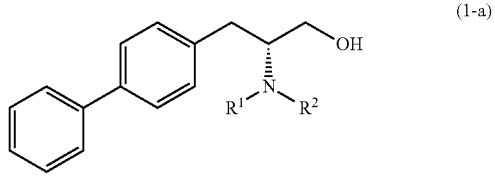
(1-a)

wherein R1 is hydrogen and R2 is tert-butoxycarbonyl, namely (R)-tert-butyl (1-([1,1-biphenyl]-4-yl)-3-hydroxy-propan-2-yl)carbamate of the following formula (1-a)*:

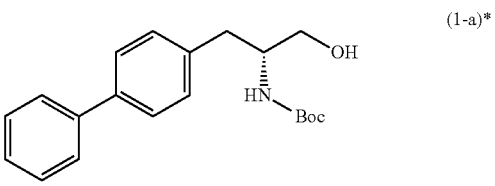 [SMILES: CC(C)(C)OC(=O)N[C@@H](CO)Cc1ccc(-c2ccccc2)cc1]
(1-a)* by reaction with di-tert-butyl dicarbonate.

In a particular embodiment of the above process, the hydrochloride salt of the compound of formula (2-a)

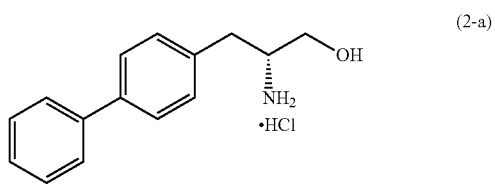 [SMILES: N[C@@H](CO)Cc1ccc(-c2ccccc2)cc1 ; Cl]
(2-a)

is obtained from a compound of formula (3-1-a)

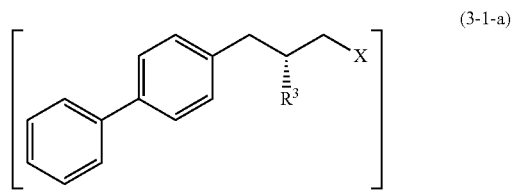
(3-1-a)

wherein X is chloro or tert-butoxy, and R3 is succinimidyl or phthalimidyl, by hydrolysis with hydrochloric acid.

One preferred embodiment to carry out this step of the invention is depicted in the following Scheme 9:

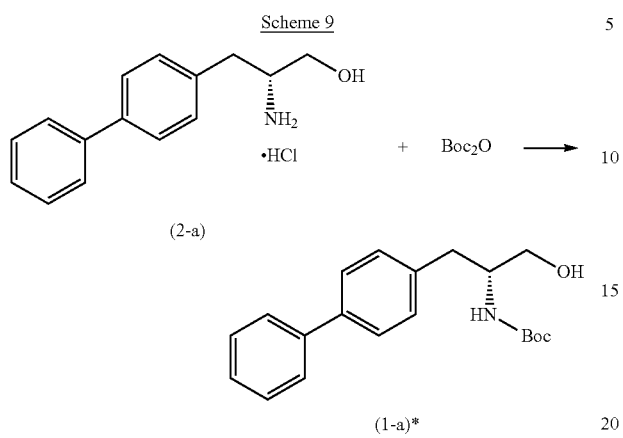

As depicted in Scheme 9, the compound of formula (2-a)—preferably obtained according to a reaction as depicted in Scheme 8—is further reacted with di-tert-butyl dicarbonate to obtain the compound of formula (1-a)*, namely (R)-tert-butyl (1-([1,1'-biphenyl]-4-yl)-3-hydroxypropan-2-yl)carbamate.

IV. Complete Sequence of the Preparation of a Compound of Formula (1-a)*

In one embodiment, the compound of formula (1-a)*, namely (R)-tert-butyl (1-([1,1-biphenyl]-4-yl)-3-hydroxypropan-2-yl)carbamate, is obtained by a reaction sequence as depicted in the following Scheme 10:

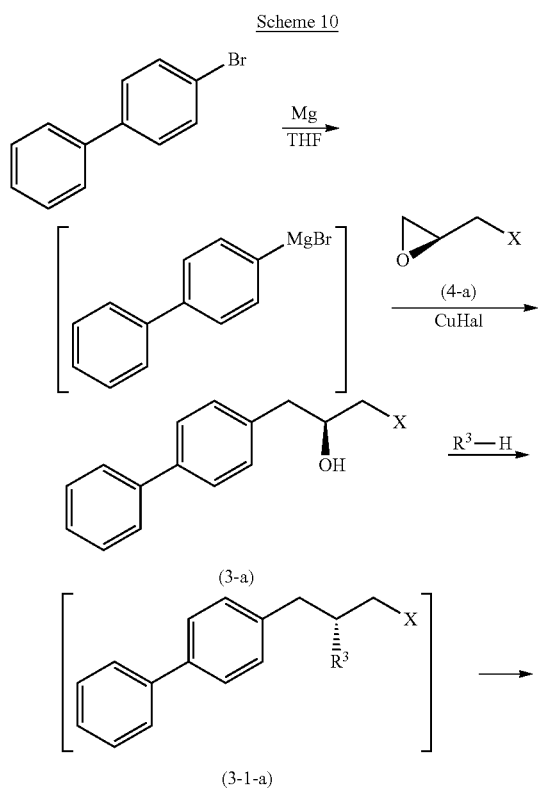

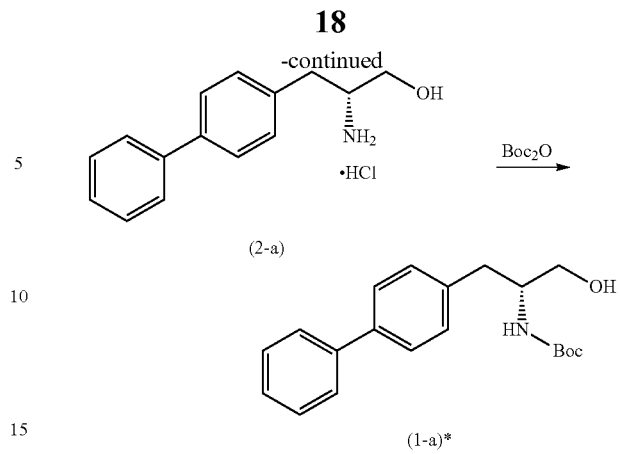

Wherein X is chloro or tert-butoxy, and R3 is succinimidyl or phthalimidyl.

As depicted in Scheme 10, in an initial two step reaction sequence, the compound of formula (3-a) is obtained by a Grignard reaction comprising reaction of 4-bromobiphenyl and metallic magnesium in tetrahydrofuran and then reacting the obtained 4-biphenylmagnesium bromide with a compound of formula (4-a), wherein X is chloro or tert-butoxy, in the presence of a cuprous (I) halide, preferably cuprous iodide, as catalyst. Then, the obtained compound of formula (3-a) wherein X is chloro or tert-butoxy is reacted under Mitsunobu conditions with an imide compound of formula R3-H selected from succinimide and phthalimide in the presence of triphenyl phosphine and a dialkyl azodicarboxylate compound in an organic solvent to deliver a compound of formula (3-1-a) wherein R3 is succinimidyl or phthalimidyl. Preferably, the dialkyl azodicarboxylate compound is diethyl azodicarboxylate (DEAD). Preferably, the organic solvent is selected from toluene, ethyl acetate, tetrahydrofurane, and dichloromethane. Then, the obtained compound of formula (3-1-a), wherein X is chloro or tert-butoxy, and R3 is succinimidyl or phthalimidyl, is hydrolysed in the presence of an inorganic acid or an inorganic base. Said inorganic acid is for example selected from hydrochloric acid and sulfuric acid; and said inorganic base is for example selected from sodium carbonate, potassium carbonate, sodium hydroxide, and potassium hydroxide. Preferably, the inorganic acid is hydrochloric acid, and the inorganic base is sodium carbonate. If the hydrolysis is carried out with the base, the obtained product is thereafter treated with hydrochloric acid in order to obtain the hydrochloride salt of the compound of formula (2-a). Finally, the compound of formula (2-a) is further reacted in a condensation reaction with di-tert-butyl dicarbonate to obtain the compound of formula (1-a), namely (R)-tert-butyl (1-([1,1'-biphenyl]-4-yl)-3-hydroxypropan-2-yl)carbamate of formula (1-a)*.

V. Further Embodiments

In another embodiment, the present invention relates to the complete reaction sequence described in Scheme 4, Scheme 5 or Scheme 6, preferably to the complete reaction sequence as described in Scheme 5.

In another embodiment the present invention in particular relates to the reaction steps as described in the preparation of a compound of formula (3) or salt thereof.

In another embodiment the present invention in particular relates to the reaction steps as described in the preparation of a compound of formula (2) or salt thereof.

In another embodiment the present invention in particular relates to the reaction steps as described in the preparation of a compound of formula (1) or salt thereof.

In another embodiment the present invention in particular relates to the reaction steps as described in the preparation of a compound of formula (3) or salt thereof plus the preparation of a compound of formula (2) or salt thereof.

In another embodiment the present invention in particular relates to the reaction steps as described in the preparation of a compound of formula (2) or salt thereof plus the preparation of a compound of formula (1) or salt thereof.

In still another embodiment, the present invention relates to the intermediate products of formula (3), of formula (3-1), of formula (2) and to the final product of formula (1).

In a preferred embodiment, the present invention relates to a compound of formula (3-a) or salt thereof in substantially optically pure form

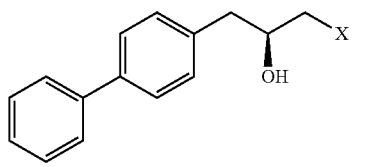

wherein X is halogen, preferably chloro, or —O—R5, wherein R5 is $C_1$-$C_6$-alkyl, preferably tert-butyl; or to a compound of formula (3-b) or salt thereof in substantially optically pure form

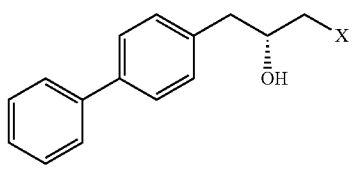

wherein X is halogen, preferably chloro, or —O—R5, wherein R5 is $C_1$-$C_6$-alkyl, preferably tert-butyl.

In another preferred embodiment, the present invention relates to a compound of formula (3-1-a) or salt thereof in substantially optically pure form

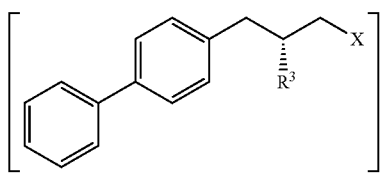

wherein R3 is an imide or azide, preferably succinimide or phthalimide, or to a compound of formula (3-1-b) or salt thereof in substantially optically pure form

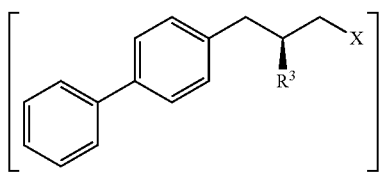

wherein R3 is an imide or azide, preferably succinimide or phthalimide.

In still another preferred embodiment, the present invention relates to a compound of formula (2-a) or salt thereof in substantially optically pure form

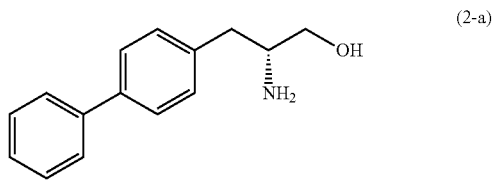 [SMILES: N[C@@H](CO)Cc1ccc(-c2ccccc2)cc1]

or to a compound of formula (2-b) or salt thereof in substantially optically pure form

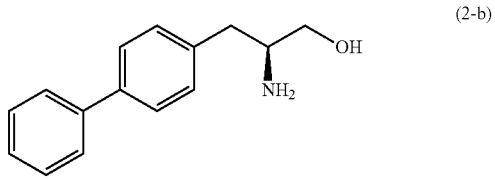 [SMILES: N[C@H](CO)Cc1ccc(-c2ccccc2)cc1]

In still another preferred embodiment, the present invention relates to a compound of formula (1-a) or salt thereof in substantially optically pure form

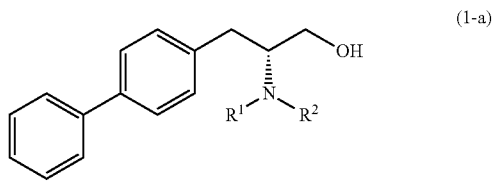

wherein R1 and R2 are, independently of each other, hydrogen or a nitrogen protecting group, wherein at least one of R1 or R2 is a nitrogen protecting group, or to a compound of formula (1-b) or salt thereof in substantially optically pure form

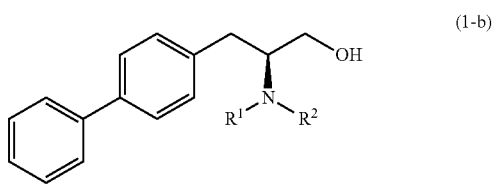

wherein R1 and R2 are, independently of each other, hydrogen or a nitrogen protecting group, wherein at least one of R1 or R2 is a nitrogen protecting group.

In one embodiment, the present invention relates to (R)-tert-butyl (1-([1,1-biphenyl]-4-yl)-3-hydroxypropan-2-yl)carbamate of the following formula (1-a)*:

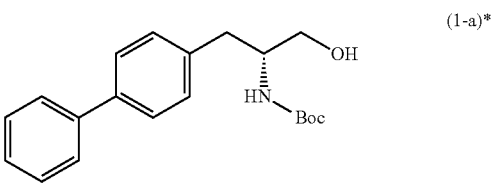 [SMILES: CC(C)(C)OC(=O)N[C@@H](CO)Cc1ccc(-c2ccccc2)cc1]

V. Follow on Reaction of a Compound of Formula (1) to Produce a NEP Inhibitor In another embodiment of the invention the products of the process of the present invention can be used in the synthesis of NEP inhibitors or salts or pro-drugs thereof, in particular they can be used in the synthesis of NEP inhibitors comprising a γ-amino-δ-biphenyl-α-methylalkanoic acid, or acid ester, backbone. NEP inhibitors or pro-drugs thereof comprising a γ-amino-δ-biphenyl-α-methylalkanoic acid, or acid ester, backbone include, for example, the NEP inhibitor pro-drug N-(3-carboxy-1-oxopropyl)-(4S)-(p-phenylphenylmethyl)-4-amino-(2R)-methylbutanoic acid ethyl ester and the corresponding NEP inhibitor N-(3-carboxy-1-oxopropyl)-(4S)-(p-phenylphenylmethyl)-4-amino-(2R)-methylbutanoic acid.

The term "NEP inhibitor" describes a compound which inhibits the activity of the enzyme neutral endopeptidase (NEP, EC 3.4.24.11).

Compounds of formula (1) or salts thereof, preferably of formula (1-a), or salts thereof, as described herein above can be oxidized to the corresponding aldehyde as described e.g. in WO 2008/138561 and then further reacted to a NEP inhibitor or salts or prodrugs thereof, in particular to the NEP inhibitor prodrug N-(3-carboxy-1-oxopropyl)-(4S)-(p-phenylphenylmethyl)-4-amino-(2R)-methylbutanoic acid ethyl ester or the corresponding NEP inhibitor N-(3-carboxy-1-oxopropyl)-(4S)-(p-phenylphenylmethyl)-4-amino-(2R)-methylbutanoic acid as described by Ksander et al. in *J. Med. Chem.* 1995, 38, 1689-1700, or as described in WO 2008/31567.

In a preferred embodiment of the invention a compound according to formula (1-a), or salt thereof, is further reacted to obtain the NEP inhibitor pro-drug N-(3-carboxy-1-oxopropyl)-(4S)-(p-phenylphenylmethyl)-4-amino-(2R)-methylbutanoic acid ethyl ester (known in the art as AHU377) or a salt thereof.

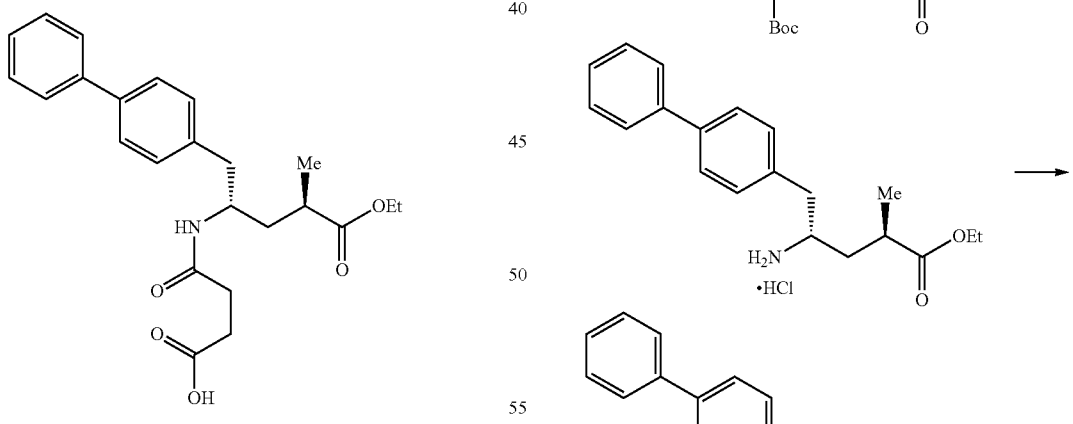

The NEP inhibitor pro-drug N-(3-carboxy-1-oxopropyl)-(4S)-(p-phenylphenylmethyl)-4-amino-(2R)-methylbutanoic acid ethyl ester optionally is further reacted to obtain the NEP inhibitor N-(3-carboxy-1-oxopropyl)-(4S)-(p-phenylphenylmethyl)-4-amino-(2R)-methylbutanoic acid.

A full reaction sequence how to obtain NEP inhibitor pro-drug N-(3-carboxy-1-oxopropyl)-(4S)-(p-phenylphenylmethyl)-4-amino-(2R)-methylbutanoic acid ethyl ester and the NEP inhibitor N-(3-carboxy-1-oxopropyl)-(4S)-(p-phenylphenylmethyl)-4-amino-(2R)-methylbutanoic acid starting from a compound of formula (1-a) with a tert-butoxycarbonyl group as nitrogen protecting group according to the procedure as described e.g. in WO 2008/138561 or WO 2008/31567 for oxidation to the corresponding aldehyde with further reaction of the aldehyde as described by Ksander et al. in *J. Med. Chem.* 1995, 38, 1689-1700, or as depicted in WO 2008/31567, is summarized in the following schemes 11 and 12, respectively:

Scheme 11

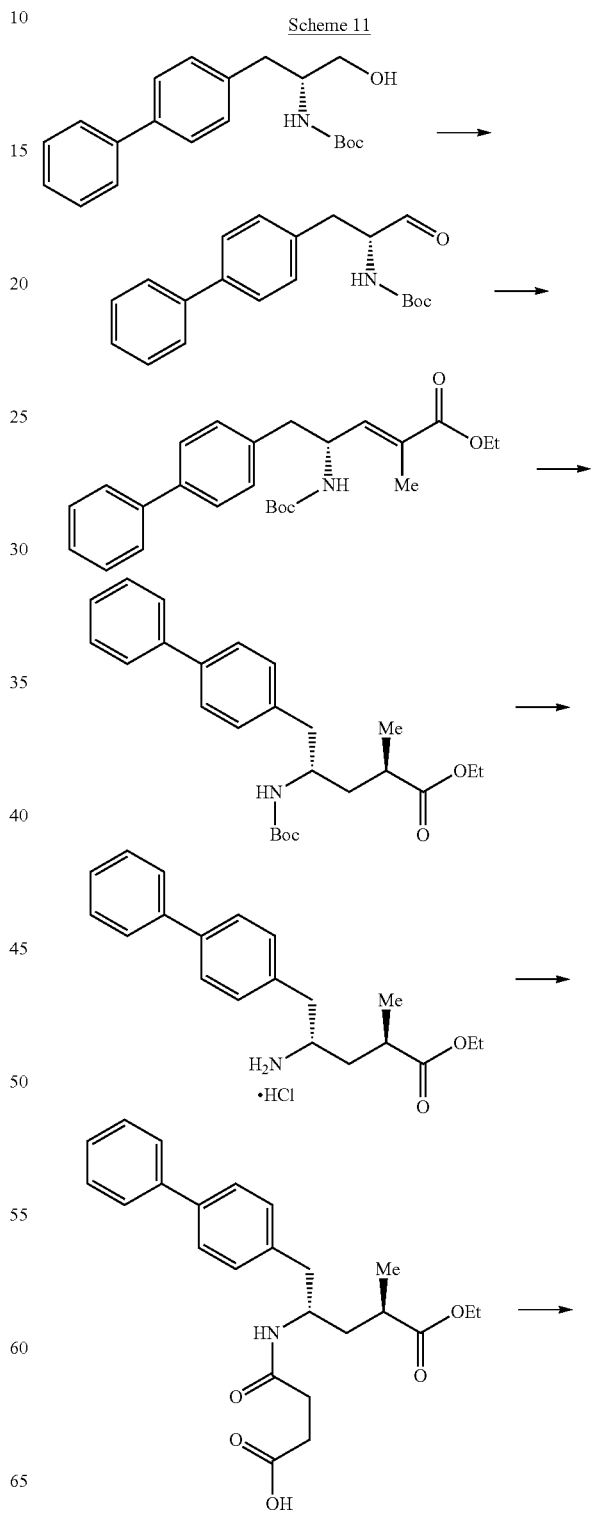

-continued

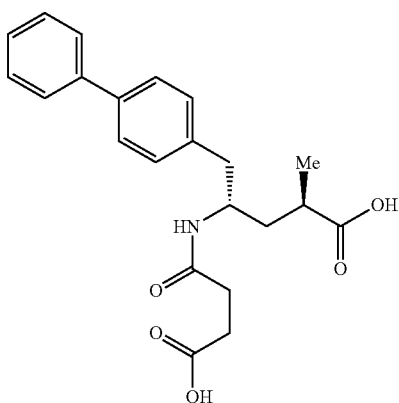 [SMILES: CCOC(=O)[C@H](C)C[C@@H](Cc1ccc(-c2ccccc2)cc1)NC(=O)CCC(=O)O]

(according to Ksander et al. in *J. Med. Chem.* 1995, 38, 1689-1700)

Scheme 12

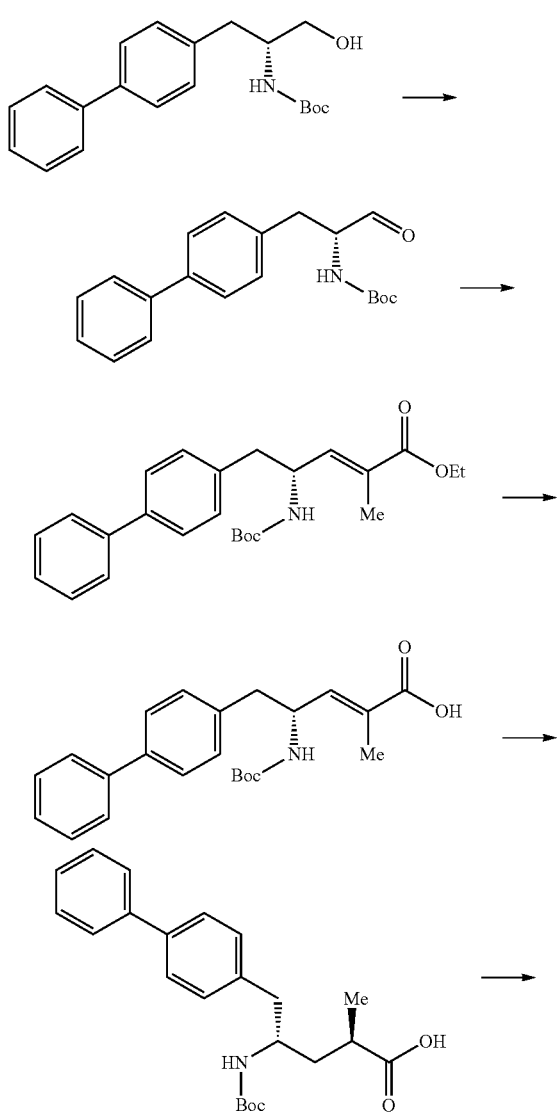

-continued

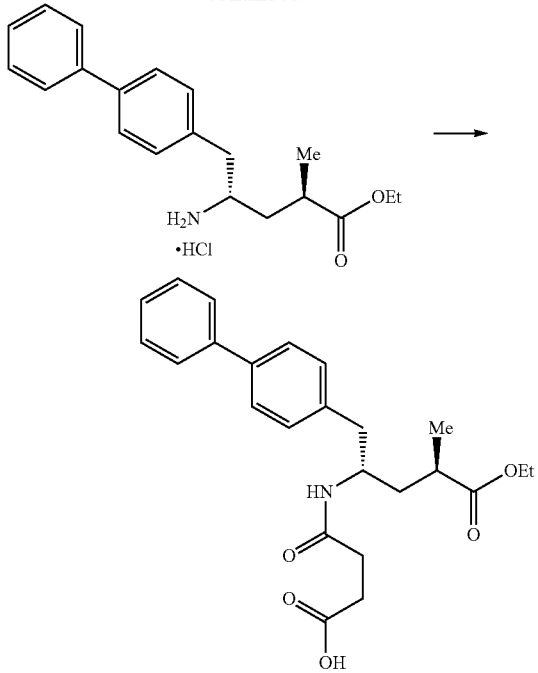

(according to WO 2008/31567)

In general, the compound of formula (1), or more specifically of formula (1-a)*, is oxidized to the corresponding aldehyde using a TEMPO mediated oxidation (WO 2008/031567) or using alternative reaction conditions, such as oxidation with Dess-Martin periodinane (see e.g. WO 2008/136561). The aldehyde is then subjected to a Wittig reaction with carbethoxyethylidene-triphenylphosphorane to deliver (R)-5-biphenyl-4-yl-4-tert-butoxycarbonylamino-2-methyl-pent-2-enoic acid ethyl ester. The ester (Scheme 11) or—after saponification of the ester—the corresponding free acid (R)-5-biphenyl-4-yl-4-tert-butoxycarbonylamino-2-methyl-pent-2-enoic acid (Scheme 12) is then hydrogenated in the presence of a catalyst, whilst preferably producing the preferred diastereoisomer with high selectivity. Deprotection of the nitrogen functionality, i.e. removal of the Boc group, —if necessary—re-introduction of the ethyl ester group, and subsequent coupling with succinic anhydride delivers the desired NEP inhibitor prodrug compound. Optionally, the ester can be saponified to the free acid providing the NEP inhibitor drug compound.

The TEMPO oxidation is carried out according to procedures known in the art, e.g. as described in G. Tojo G and M. I. Fernandez "Oxidation of Primary Alcohols to Carboxylic Acids. A guide to current common practice", 2007, Chapter 6 "TEMPO mediated oxidations", and Janssen et al. "Towards greener solvents for the bleach oxidation of alcohols catalysed by stable N-oxy radicals" Green Chem. 2011, 13, 905-912.

One molar equivalent of the alcohol (R)-tert-butyl (1-([1,1-biphenyl]-4-yl)-3-hydroxypropan-2-yl)carbamate and 0.5 to 3, preferably 1 to 2, more preferably about 1, 1.25, 1.5, 1.9 or 2 molar equivalents of NaBr, and 0.5 to 3, preferably 1 to 2, more preferably 1.0, 1.25 or 1.5, in particular 1.5 equivalents of NaHCO$_3$ and a biphasic buffered solvent system (e.g. a mixture of water and isopropyl acetate in an about 2:1 molar ratio or a ratio of about 3:1 VN) are added together, mixed vigorously and stirred until dissolution. The mixture is cooled down to 0-5° C. before addition of about 0.002 to 0.1, preferably 0.01 to 0.05, more preferably about 0.02 equivalents of the TEMPO catalyst, and of 1 to 8, preferably 1 to 5, more preferably about 1 to 2, most preferred about 1.0, 1.25, or 1.5, in particular 1.45 equivalents of the oxidant NaClO, preferably in the form of a 2 to 20% w/w (of active chlorine) solution, more preferably in the form of a 4 to 15% w/w (of active chlorine) solution, and most preferably in the form of a 8 to 12% w/w (of active chlorine) solution. The mixture is stirred while keeping the temperature at 0-5° C. until all starting alcohol is used up. Then, the reaction mixture is quenched by addition of an aqueous solution of sodium thiosulfate while warming the temperature to 20-25° C. The phases are separated and the recovered organic phase with the aldehyde (R)-tert-butyl (1-([1,1-biphenyl]-4-yl)-3-oxopropan-2-yl)carbamate is directly used in the subsequent Wittig reaction. Optionally, the organic layer can be worked-up by washing with aqueous NaHCO₃ solution and/or aqueous NaCl solution.

Accordingly, in another embodiment the present invention relates to a process for preparing a compound of formula (5), or a salt thereof,

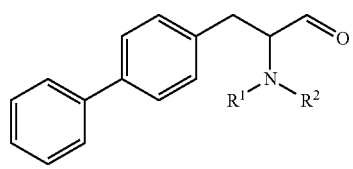

(5)

wherein R1 and R2 are, independently of each other, hydrogen or a nitrogen protecting group and at least one of R1 or R2 is a nitrogen protecting group,
preferably wherein the compound of formula (5) is of formula (5-a)

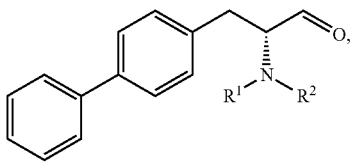

(5-a)

more preferably wherein the compound of formula (5-a) is of formula (5-a)*

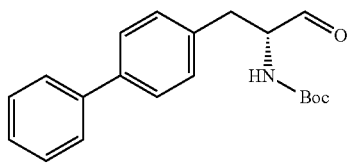

(5-a)* by oxidizing a compound of formula (1) or salt thereof

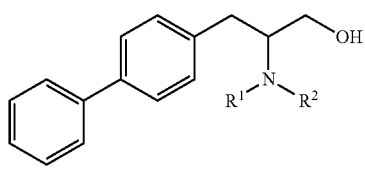

(1)

wherein R1 and R2 are, independently of each other, hydrogen or a nitrogen protecting group, wherein at least one of R1 or R2 is a nitrogen protecting group,
preferably a compound of formula (1-a) or salt,

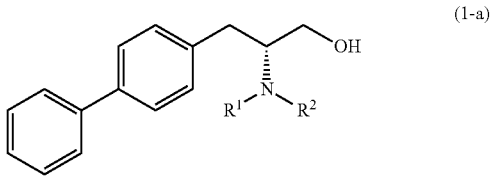

(1-a)

wherein R1 and R2 are, independently of each other, hydrogen or a nitrogen protecting group, wherein at least one of R1 or R2 is a nitrogen protecting group,
more preferably the compound (R)-tert-butyl (1-([1,1-biphenyl]-4-yl)-3-hydroxypropan-2-yl)carbamate of formula (1-a)*

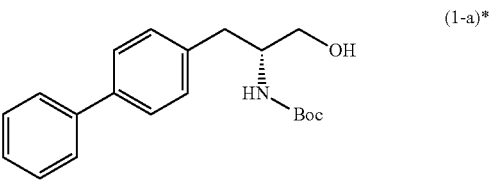 [SMILES: CC(C)(C)OC(=O)N[C@@H](CO)Cc1ccc(-c2ccccc2)cc1]

(1-a)* in a TEMPO mediated oxidation reaction to obtain a compound of formula (5) or salt thereof, preferably of formula (5-a) or salt thereof, more preferably a compound of formula (5-a)*.

In one embodiment, this step delivering the compound of formula (5) is carried out after the processes described here within, which results in the production of a compound of formula (1).

In a preferred embodiment thereof, the TEMPO mediated oxidation is carried out in the presence of NaBr, NaHCO₃, NaClO, and a catalytic amount of the TEMPO catalyst, in a biphasic buffered solvent system. Preferably, the biphasic solvent system comprises water and isopropyl acetate, preferably in an about 2:1 molar ratio or a ratio of about 3:1 VN. Preferably, the reagents are added stepwise, by first adding NaBr and NaHCO₃, and secondly the catalytic amount of the TEMPO catalyst and finally the NaClO solution.

In one embodiment, the molar ratios of the reagents are:
1 equivalent of the compound of formula (1), formula (1-a) or (1-a)*,
0.5 to 3, preferably 1 to 2, more preferably about 1, 1.25, 1.5, 1.9 or 2 molar equivalents of NaBr,
0.5 to 3, preferably 1 to 2, more preferably 1.0, 1.25 or 1.5 equivalents of NaHCO₃
0.002 to 0.1, preferably 0.01 to 0.05, more preferably about 0.02 equivalents of the TEMPO catalyst, and
1 to 8, preferably 1 to 5, more preferably about 1 to 2, most preferred about 1.0, 1.25, or 1.5, in particular 1.45 equivalents of the oxidant NaClO, preferably in the form of a 2 to 20% w/w (of active chlorine) solution, more preferably in the form of a 4 to 15% w/w (of active chlorine) solution, most preferably in the form of a 8 to 12% w/w (of active chlorine) solution, in particular in the form of a 12% w/w (of active chlorine) solution.

General Terms:

The general definitions used above and below, unless defined differently, have the following meanings:

The term "nitrogen protecting group" comprises any group which is capable of reversibly protecting a nitrogen functionality, preferably an amine and/or amide functionality. Preferably the nitrogen protecting group is an amine protecting group and/or an amide protecting group. Suitable nitrogen protecting groups are conventionally used e.g. in peptide chemistry and are described e.g. in the relevant chapters of standard reference works such as J. F. W. McOmie, "Protective Groups in Organic Chemistry", Plenum Press, London and New York 1973, in P. G. M. Wuts and T. W. Greene, "Greene's Protective Groups in Organic Synthesis', fourth edition, Wiley, N.J., 2007, and "The Peptides"; volume 3 (editors: E. Gross and J. Meienhofer), Academic Press, London and New York 1981, and "Methoden der organischen Chemie" (Methods of Organic Chemistry), Houben Weyl, fourth edition, volume 15/I, Georg Thieme Verlag, Stuttgart 1974.

Preferred nitrogen protecting groups generally comprise: unsubstituted or substituted $C_1$-$C_6$-alkyl, preferably $C_1$-$C_4$-alkyl, more preferably $C_1$-$C_2$-alkyl, most preferably $C_1$-$C_6$-alkyl, unsubstituted or substituted $C_{2-4}$-alkenyl, wherein $C_1$-$C_6$-alkyl and $C_{2-4}$-alkenyl is optionally mono-, di- or tri-substituted by trialkylsilyl-$C_1$-$C_7$-alkoxy (e.g. trimethylsilylethoxy), cycloalkyl, aryl, preferably phenyl, or a heterocyclic group, preferably pyrrolidinyl, wherein the cycloalkyl group, the aryl ring or the heterocyclic group is unsubstituted or substituted by one or more, e.g. two or three residues, e.g. selected from the group consisting of $C_1$-$C_7$-alkyl, hydroxy, $C_1$-$C_7$-alkoxy, $C_2$-$C_8$-alkanoyl-oxy, halogen, nitro, cyano, and $CF_3$; aryl-$C_1$-$C_2$-alkoxycarbonyl (preferably phenyl-$C_1$-$C_2$-alkoxycarbonyl e.g. benzyloxycarbonyl); $C_{1-10}$-alkenyloxycarbonyl; $C_{1-6}$-alkylcarbonyl (e.g. acetyl or pivaloyl); $C_{6-10}$-arylcarbonyl; $C_{1-6}$-alkoxycarbonyl (e.g. tert-butoxycarbonyl); $C_{6-10}$-aryl-$C_{1-6}$-alkoxycarbonyl; allyl or cinnamyl; sulfonyl or sulfenyl; succinimidyl group, silyl, e.g. triarylsilyl or trialkylsilyl (e.g. triethylsilyl).

Examples of preferred nitrogen protecting groups are acetyl, benzyl, cumyl, benzhydryl, trityl, benzyloxycarbonyl (Cbz), 9-fluorenylmethyloxycarbony (Fmoc), benzyloxymethyl (BOM), pivaloyl-oxy-methyl (POM), trichloroethxoycarbonyl (Troc), 1-adamantyloxycarbonyl (Adoc), allyl, allyloxycarbonyl, trimethylsilyl, tert-butyl-dimethylsilyl (TBDMS), triethylsilyl (TES), triisopropylsilyl (TIPS), trimethylsilyethoxymethyl (SEM), tert-butoxycarbonyl (BOC), tert-butyl, 1-methyl-1,1-dimethylbenzyl, (phenyl) methylbenzene, pyrridinyl and pivaloyl. Most preferred nitrogen protecting groups are acetyl, benzyl, benzyloxycarbonyl (Cbz), triethylsilyl (TES), trimethylsilyethoxymethyl (SEM), tert-butoxycarbonyl (BOC), pyrrolidinylmethyl and pivaloyl.

Examples of more preferred nitrogen protecting groups are tert-butoxycarbonyl (BOC), benzoyl, styryl, 1-butenyl, benzyl, p-methoxybenzyl (PMB) and pyrrolidinylmethyl.

Silyl, as used herein, refers to a group according to the formula —SiR11R12R13, wherein R11, R12 and R13 are, independently of each other, alkyl or aryl. Preferred examples for R11, R12 and R13 are methyl, ethyl, isopropyl, tert-butyl, phenyl or phenyl-$C_{1-4}$-alkyl.

Alkyl is defined as a radical or part of a radical as a straight or branch (one or, if desired and possible, more times) carbon chain, and is especially $C_1$-$C_7$-alkyl, preferably $C_1$-$C_4$-alkyl.

The term "$C_1$-$C_7$-" defines a moiety with up to and including maximally 7, especially up to and including maximally 4, carbon atoms, said moiety being branched (one or more times) or straight-chained and bound via a terminal or a non-terminal carbon.

Cycloalkyl is, for example, $C_3$-$C_7$-cycloalkyl and is, for example, cyclopropyl, cyclobutyl, cyclopentyl, cyclohexyl and cycloheptyl. Cyclopentyl and cyclohexyl are preferred.

Alkoxy is, for example, $C_1$-$C_7$-alkoxy and is, for example, methoxy, ethoxy, n-propyloxy, isopropyloxy, n-butyloxy, isobutyloxy, sec-butyloxy, tert-butyloxy and also includes corresponding pentyloxy, hexyloxy and heptyloxy radicals. $C_1$-$C_4$-alkoxy is preferred.

Alkanoyl is, for example, $C_2$-$C_8$-alkanoyl and is, for example, acetyl [—C(=O)Me], propionyl, butyryl, isobutyryl or pivaloyl. $C_2$-$C_5$-Alkanoyl is preferred, especially acetyl.

Halo or halogen is preferably fluoro, chloro, bromo or iodo, most preferably, chloro, bromo, or iodo.

Halo-alkyl is, for example, halo-$C_1$-$C_7$-alkyl and is in particular halo-$C_1$-$C_4$-alkyl, such as trifluoromethyl, 1,1,2-trifluoro-2-chloroethyl or chloromethyl. Preferred halo-$C_1$-$C_7$-alkyl is trifluoromethyl.

Alkenyl may be linear or branched alkyl containing a double bond and comprising preferably 2 to 12 carbon atoms, 2 to 10 carbon atoms being especially preferred. Particularly preferred is a linear $C_{2-4}$-alkenyl. Some examples of alkyl groups are ethyl and the isomers of propyl, butyl, pentyl, hexyl, heptyl, octyl, nonyl, decyl, undecyl, dodecyl, tetradecyl, hexadecyl, octacyl and eicosyl, each of which containing a double bond. Especially preferred is allyl.

Alkylene is a bivalent radical derived from $C_{1-7}$-alkyl and is especially $C_2$-$C_7$-alkylene or $C_2$-$C_7$-alkylene and, optionally, can be interrupted by one or more, e.g. up to three oxygen, NR14 or sulfur, wherein R14 is alkyl, each of which can be unsubstituted or substituted, by one or more substituents independently selected from for example, $C_1$-$C_7$-alkyl, $C_1$-$C_7$-alkoxy-$C_1$-$C_7$-alkyl or $C_1$-$C_7$-alkoxy.

Alkenylene is a bivalent radical derived from $C_{2-7}$-alkenyl and can be interrupted by one or more, e.g. up to three oxygen, NR14 or sulfur, wherein R14 is alkyl, and is unsubstituted or substituted by one or more, e.g. up to three substitutents, preferably independently selected from the substituents mentioned above for alkylene.

Aryl being a radical or part of a radical is, for example $C_{6-10}$-aryl, and is preferably a mono- or polycyclic, especially monocyclic, bicyclic or tricyclic aryl moiety with 6 to 10 carbon atoms, preferably phenyl, and which can be unsubstituted or substituted, by one or more substituents, independently selected from, e.g. $C_1$-$C_7$-alkyl, $C_1$-$C_7$-alkoxy-$C_1$-$C_7$-alkyl or $C_1$-$C_7$-alkoxy.

The term arylalkyl refers to aryl-$C_1$-$C_7$-alkyl, wherein aryl is as defined herein and is for example benzyl.

The term carboxyl refers to —$CO_2H$.

Aryloxy refers to an aryl-O— wherein aryl is as defined above.

Unsubstituted or substituted heterocyclyl is a mono- or polycyclic, preferably a mono-, bi- or tricyclic-, most preferably mono-, unsaturated, partially saturated, saturated or aromatic ring system with preferably 3 to 14 (more preferably 5 to 14) ring atoms and with one or more, preferably one to four, heteroatoms, independently selected from nitrogen, oxygen, sulfur, S(=O)— or S—(=O)$_2$, and is unsubstituted or substituted by one or more, e.g. up to three substitutents, preferably independently selected from the group consisting of halo, $C_1$-$C_7$-alkyl, halo-$C_1$-$C_7$-alkyl, $C_1$-$C_7$-alkoxy, halo-$C_1$-$C_7$-alkoxy, such as trifluoromethoxy and $C_1$-$C_7$-alkoxy-$C_1$-$C_7$-alkoxy. When the heterocyclyl is an aromatic ring system, it is also referred to as heteroaryl.

Acetyl is —C(═O)$C_1$-$C_7$-alkyl, preferably —C(═O)Me.

Sulfonyl is (unsubstituted or substituted) $C_1$-$C_7$-alkylsulfonyl, such as methylsulfonyl, (unsubstituted or substituted) phenyl- or naphthyl-$C_1$-$C_7$-alkylsulfonyl, such as phenylmethanesulfonyl, or (unsubstituted or substituted) phenyl- or naphthyl-sulfonyl; wherein if more than one substituent is present, e.g. one to three substitutents, the substituents are selected independently from cyano, halo, halo-$C_1$-$C_7$-alkyl, halo-$C_1$-$C_7$-alkyloxy- and $C_1$-$C_7$-alkyloxy. Especially preferred is $C_1$-$C_7$-alkylsulfonyl, such as methylsulfonyl, and (phenyl- or naphthyl)-$C_1$-$C_7$-alkylsulfonyl, such as phenylmethanesulfonyl.

Sulfenyl is (unsubstituted or substituted) $C_{6-10}$-aryl-$C_1$-$C_7$-alkylsulfenyl or (unsubstituted or substituted) $C_{6-10}$-arylsulfenyl, wherein if more than one substituent is present, e.g. one to four substitutents, the substituents are selected independently from nitro, halo, halo-$C_1$-$C_7$-alkyl and $C_1$-$C_7$-alkyloxy.

Imide refers to a (unsubstituted or substituted) functional group consisting of two acyl groups bound to nitrogen, preferably a cyclic group derived from dicarboxylic acids. Especially preferred is succinimidyl derived from succinic acid or phthalimidyl derived from phthalic acid. The imidyl group may be substituted by one or more substituents independently selected from for example, $C_1$-$C_7$-alkyl, $C_1$-$C_7$-alkoxy-$C_1$-$C_7$-alkyl, $C_1$-$C_7$-alkoxy or halo.

Azide refers to a group —N═N$^+$═N$^-$.

The term "chiral" refers to molecules which have the property of non-superimposability on their mirror image partner, while the term "achiral" refers to molecules which are superimposable on their mirror image partner.

In the formulae of the present application the term "⁓" on a C-sp$^3$ represents a covalent bond, wherein the stereochemistry of the bond is not defined. This means that the term "⁓" on a C-sp$^3$ comprises an (S) configuration as well as an (R) configuration of the respective chiral centre. Furthermore, mixtures, e.g. mixtures of enantiomers such as racemates, are also encompassed by the present invention.

In the formulae of the present application the term "⁓" on a C-sp$^2$ represents a covalent bond, wherein the stereochemistry or the geometry of the bond is not defined. This means that the term "⁓" on a C-sp$^2$ comprises a (Z) configuration as well as a (E) configuration of the respective double bond. Furthermore, mixtures, e.g., mixtures of double bond isomers are also encompassed by the present invention.

The compounds of the present invention can possess one or more asymmetric centers. The preferred absolute configurations are as indicated herein specifically.

In the formulae of the present application the term "╱" on a C-sp$^3$ indicates the absolute stereochemistry, either (R) or (S).

In the formulae of the present application the term "╱" on a C-sp$^3$ indicates the absolute stereochemistry, either (R) or (S).

In the formulae of the present application, the term "╌╌╌╌╌╌╌╌╌" indicates a C-sp$^3$-C-sp$^3$ bond or a C-sp$^2$-C-sp$^2$ bond.

The term "substantially optically pure" compound, as defined herein, refers to a compound obtained by a process according to the invention wherein the compound has an optical purity of at least 70% (ee=enantiomeric excess), more preferably of at least 90% (e.e.) and most preferably at least 95% (ee) or more, such as 100% (ee).

Salts are especially pharmaceutically acceptable salts or generally salts of any of the intermediates mentioned herein, except if salts are excluded for chemical reasons the skilled person will readily understand. They can be formed where salt forming groups, such as basic or acidic groups, are present that can exist in dissociated form at least partially, e.g. in a pH range from 4 to 10 in aqueous solutions, or can be isolated especially in solid, especially crystalline, form.

Such salts are formed, for example, as acid addition salts, preferably with organic or inorganic acids, from compounds or any of the intermediates mentioned herein with a basic nitrogen atom (e.g. imino or amino), especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane-sulfonic acid, ethane-1,2-disulfonic acid, benzene-sulfonic acid, 2-naphthalenesulfonic acid, 1,5-naphthalene-disulfonic acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or NN-dimethyl-piperazine.

When a basic group and an acid group are present in the same molecule, any of the intermediates mentioned herein may also form internal salts.

For isolation or purification purposes of any of the intermediates mentioned herein it is also possible to use pharmaceutically unacceptable salts, for example picrates or perchlorates.

In view of the close relationship between the compounds and intermediates in free form and in the form of their salts, including those salts that can be used as intermediates, for example in the purification or identification of the compounds or salts thereof, any reference to "compounds", "starting materials" and "intermediates" hereinbefore and hereinafter is to be understood as referring also to one or more salts thereof or a mixture of a corresponding free compound, intermediate or starting material and one or more salts thereof, each of which is intended to include also any solvate or salt of any one or more of these, as appropriate and expedient and if not explicitly mentioned otherwise. Different crystal forms may be obtainable and then are also included.

Where the plural form is used for compounds, starting materials, intermediates, salts, pharmaceutical preparations, diseases, disorders and the like, this intends to mean one (preferred) or more single compound(s), salt(s), pharmaceutical preparation(s), disease(s), disorder(s) or the like, where the singular or the indefinite article ("a", "an") is used, this does not intend to exclude the plural, but only preferably means "one".

The term "pro-drug", as used herein, represents in particular compounds which are transformed in vivo to the parent compound, for example, by hydrolysis in blood, for example as described in T. Higuchi and V. Stella, "Pro-drugs as Novel Delivery Systems", volume 14 of the ACS Symposium Series; Edward B. Roche, editor, "Bioreversible Carriers in Drug Design", American Pharmaceutical Association and Pergamon Press, 1987; H Bundgaard, editor, "Design of Prodrugs", Elsevier, 1985; Judkins et al. *Synthetic Communications* 1996, 26, 4351-4367, and "The Organic Chemistry of Drug Design and Drug Action", second edition, R. B. Silverman (particularly chapter 8, pages 497-557), Elsevier Academic Press, 2004.

Pro-drugs therefore include drugs having a functional group which has been transformed into a reversible derivative thereof. Typically, such prodrugs are transformed to the active drug by hydrolysis. As examples may be mentioned the following:

| Functional Group | Reversible derivative |
|---|---|
| Carboxylic acid | Esters, including e.g. alkyl esters |
| Alcohol | Esters, including e.g. sulfates and phosphates as well as carboxylic acid esters |
| Amine | Amides, carbamates, imines, enamines, |
| Carbonyl (aldehyde, ketone) | Imines, oximes, acetals/ketals, enol esters, oxazolidines and thiazoxolidines |

Pro-drugs also include compounds convertible to the active drug by an oxidative or reductive reaction. As examples may be mentioned:
Oxidative Activation
N- and O-dealkylation
Oxidative deamination
N-oxidation
Epoxidation
Reductive Activation
Azo reduction
Sulfoxide reduction
Disulfide reduction
Bioreductive alkylation
Nitro reduction Each of the above described reactions and/or reaction steps can be used individually or in combination in a method to prepare a NEP-inhibitor or a prodrug thereof, such as a NEP inhibitor or pro-drug thereof comprising a γ-amino-δ-biphenyl-α-methylalkanoic acid, or acid ester, such as alkyl ester, backbone. In particular the NEP-inhibitor is N-(3-carboxy-1-oxopropyl)-(4S)-(p-phenylphenylmethyl)-4-amino-(2R)-methylbutanoic acid or a salt thereof or a pro-drug thereof.

EXAMPLES

The following examples serve to illustrate the invention without limiting the scope thereof, while they on the other hand represent preferred embodiments of the reaction steps, intermediates and/or the process of the present invention.

ABBREVIATIONS

δ chemical shift
μl microliter
Ac acetyl
Bn benzyl
Boc tert-butoxycarbonyl
$BOC_2O$ di-tert-butyl carbonate
Cbz benzyl carbamate
Cbz-Cl benzyl chloroformate
DCM dichloromethane/methylenechloride
de diastereomeric excess
DMAP 4-(dimethylamino)pyridine
DMF N,N-dimethylformamide
DMPU 1,3-dimethyl-3,4,5,6-tetrahydro-2(1H)-pyrimidinone
DMSO dimethylsulfoxide
ee enantiomeric excess
ES electrospray
ESI electrospray ionisation
Et ethyl
EtOAc ethyl acetate
h hour(s)
HNMR proton nuclear magnetic resonance
HOBt 1-hydroxybenzotriazole
HPLC high performance liquid chromatography
i-Pr isopropyl
iPrOAc isopropyl acetate
IR infra red
KHMDS potassium bis(trimethylsilyl)amide
L liter
LC-MS liquid chromatography-mass spectrometry
LDA lithium diisopropylamide
LHMDS lithium bis(trimethylsilyl)amide
M molarity
m/e mass-to-charge ratio
Me methyl
mg milligram
min minute(s)
mL milliliter
mmol(s) millimole(s)
mol(s) mole(s)
MS mass spectrometry
NaHMDS sodium bis(trimethylsilyl)amide
nm nanometer
NMR nuclear magnetic resonance
Pd/C palladium on carbon
Ph phenyl
Piv pivaloyl
Piv-Cl pivaloyl chloride
ppm parts per million
psi pounds per square inch
RT room temperature
SEM 2-(trimethylsilyl)ethoxymethyl
SEM-Cl (2-chloromethoxyethyl)-trimethylsilane
TEMPO (2,2,6,6-tetramethyl-piperidin-1-yl)oxidanyl
TES triethylsilyl
TFA trifluoroacetic acid
THF tetrahydrofuran
TLC thin layer chromatography
TMEDA N,N,N',N'-tetramethylethylenediamine
$t_R$ retention time
Ts tosyl
TsO tosylate In quoting NMR data, the following abbreviations are used: s, singlet; d, doublet; t, triplet; q, quartet; quint., quintet; m, multiplet.

Example 1

The following examples describe the synthesis of compounds falling under general formula (3) according to the following general reaction

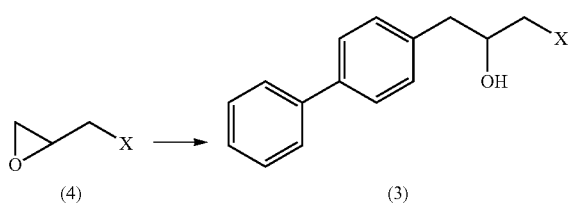

wherein X is halogen, preferably chloro, or —O—R5, wherein R5 is $C_1$-$C_6$-alkyl, preferably tert-butyl, and wherein the compound of formula (4) is reacted with a biphenylic compound, preferably an activated biphenylic compound.

Example 1A (S)-1-([1,1'-biphenyl]-4-yl)-3-chloropropan-2-ol

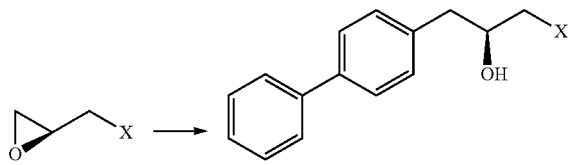

Example 1A-1

(S)-1-([1,1'-biphenyl]-4-yl)-3-chloropropan-2-ol (lab scale)

4.94 g magnesium powder in 88 g THF were added to a 500 ml four-neck flask, and stirred. In parallel, a solution of 46.6 g 4-bromobiphenyl in 88 g THF was prepared. The reaction system was heated to 35-45° C. under vacuum and $N_2$ atmosphere. To the magnesium/THF mixture, a small amount of iodine and 25 ml of the 4-bromobiphenyl solution in THF was added whilst stirring. Then, the rest of the 4-bromobiphenyl solution in THF was added at 35-45° C. whilst maintaining the temperature. After the mixture was cooled down, 3.81 g cuprous iodide was added and the mixture was further cooled down. Then, a solution of 22.2 g (S)-epichlorohydrine in 30 g THF was added at −15 to −20° C. whilst maintaining the temperature. Then the mixture was dropped into 120.4 g 4 M hydrochloric acid and stirred. Then, the mixture was allowed to stand to separate into the phases. The organic phase was collected, and the water phase extracted with THF. The combined organic phase were washed with a saturated solution of NaCl, and concentrated at reduced pressure at an internal temperature of about 35-40° C. The solids were isolated by filtration, and the filter cake was washed with purified water and dried at about 55-60° C. under vacuum to give 45.4 g of the title compound.

$[\alpha]_D^{25}$ +9.334. (c=0.01 g/ml, $CHCl_3$)

$^1$H-NMR (600 MHz, $CDCl_3$) δ 2.26 (dd, J=5.2, 0.8 Hz, 1H, OH), 2.97 (d, J=6.6 Hz, 2H, $CH_2$), 3.57 (dd, J=11.2, 6.4 Hz, 1H, $CH_2$), 3.69 (dd, J=10.8, 4.0 Hz, 1H, $CH_2$), 4.11-4.15 (m, 1H, CH), 7.33-7.45 (m, 3H, Ar—H), 7.47 (d, J=7.6 Hz, 2H, Ar—H), 7.57-7.62 (m, 4H, Ar—H).

The same reaction as under Example 1A-1 was carried out using 3.81 g cuprous bromide and 3.81 g cuprous chloride instead of the 3.81 g cuprous iodide, delivering 47.6 g and 47.0 g of the title compound, respectively.

Example 1A-2

(S)-1-([1,1'-biphenyl]-4-yl)-3-chloropropan-2-ol (industrial scale)

A mixture of 5.3 kg magnesium powder in 95 kg THF was heated to about 45-50° C. In parallel a solution of 50 kg 4-bromobiphenyl in 95 kg THF was prepared. To the magnesium/THF mixture 0.2 kg iodine and about 10% of the 4-bromobiphenyl solution was added. At about 45-50° C. the rest of the 4-brombiphenyl solution was slowly added during about 2-2.5 h. After further 2.5-3 h at this temperature the mixture was cooled down to about 0-5° C. Then 4 kg cuprous iodide was added and the mixture cooled down to about −15 to −20° C. After 30 min a solution of 56 kg (S)-epichlorohydrin in 100 kg THF was added at about −15 to −20° C. The temperature was maintained for about 4 h. Then the mixture was dropped into 32.6 kg 36% hydrochloric acid in 310 kg $H_2O$ at about 10° C. After 30 min at about 10° C., the mixture was then allowed to warm to about 20-25° C., and the phases are separated. The organic phase was concentrated at reduced pressure at an internal temperature of about 35-40° C. until the mixture becomes sticky. Then additional 210 kg $H_2O$ was added and the concentration of the organic layer was continued until no further distillate comes over. The resulting suspension was cooled down to about 10-15° C. and stirred for 1 h. The solids were isolated by filtration, the filter cake was washed twice with 2×100 kg $H_2O$ and dried at about 50-60° C. under vacuum to give 48.7 kg (S)-1-([1,1'-biphenyl]-4-yl)-3-chloropropan-2-ol (90-95% purity by HPLC, 99% ee).

Melting point: 136-137° C.

MS (ESI, m/e) 246.73.

$[\alpha]_D^{25}$ +9.334 (c=0.01 g/ml, $CHCl_3$)

$^1$H-NMR (600 MHz, $CDCl_3$) δ 2.26 (dd, J=5.2, 0.8 Hz, 1H, OH), 2.97 (d, J=6.6 Hz, 2H, $CH_2$), 3.57 (dd, J=11.2, 6.4 Hz, 1H, $CH_2$), 3.69 (dd, J=10.8, 4.0 Hz, 1H, $CH_2$), 4.11-4.15 (m, 1H, CH), 7.33-7.45 (m, 3H, Ar—H), 7.47 (d, J=7.6 Hz, 2H, Ar—H), 7.57-7.62 (m, 4H, Ar—H).

Example 1B (S)-1-([1,1'-biphenyl]-4-yl)-3-tert-butoxypropan-2-ol

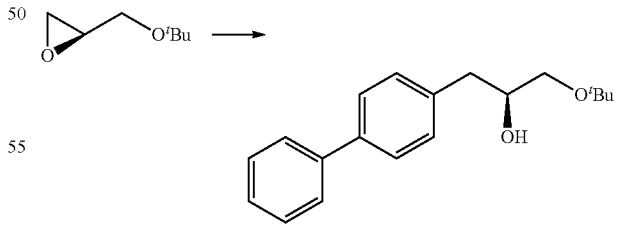

4.94 g magnesium powder in 88 g THF were added to a 500 ml four-neck flask, and stirred. In parallel, a solution of 46.6 g 4-bromobiphenyl in 88 g THF was prepared. The reaction system was heated to 35-45° C. under vacuum and $N_2$ atmosphere. To the magnesium/THF mixture, a small amount of iodine and 25 ml of the 4-bromobiphenyl solution in THF was added whilst stirring. Then, the rest of the 4-bromobiphenyl solution in THF was added at 35-45° C.

whilst maintaining the temperature. After the mixture was cooled down, 3.81 g cuprous iodide was added and the mixture was further cooled down. Then, a solution of 22.2 g (S)-epoxy-tert-butylether in 30 g THF was added at −15 to −20° C. whilst maintaining the temperature. Then the mixture was dropped into 120.4 g 4 M hydrochloric acid and stirred. Then, the mixture was allowed to stand to separate into the phases. The organic phase was collected, and the water phase extracted with THF. The combined organic phase were washed with a saturated solution of NaCl, and concentrated at reduced pressure at an internal temperature of about 35-40° C. The solids were isolated by filtration, and the filter cake was washed with purified water and dried at about 55-60° C. under vacuum to give 51.7 g of the title compound.

$[\alpha]_D^{25}$ +10.933 (c=0.01 g/ml, CHCl$_3$)

$^1$H-NMR (400 MHz, CDCl$_3$) δ 1.22 (s, 9H, CH$_3$), 2.55 (s, 1H, OH), 2.80-2.90 (m, 2H, CH$_2$), 3.28 (dd, J=8.8, 7.2 Hz, 1H, CH$_2$), 3.43 (dd, J=8.8, 3.6 Hz, 1H, CH$_2$), 3.97-4.03 (m, 1H, CH), 7.31-7.36 (m, 3H, Ar—H), 7.42-7.46 (m, 2H, Ar—H), 7.54 (d, J=8.0 Hz, 2H, Ar—H), 7.59-7.61 (m, 2H, Ar—H).

Example 2

The following examples describe the synthesis of compounds of formula (2) or salts thereof according to the following general reaction scheme

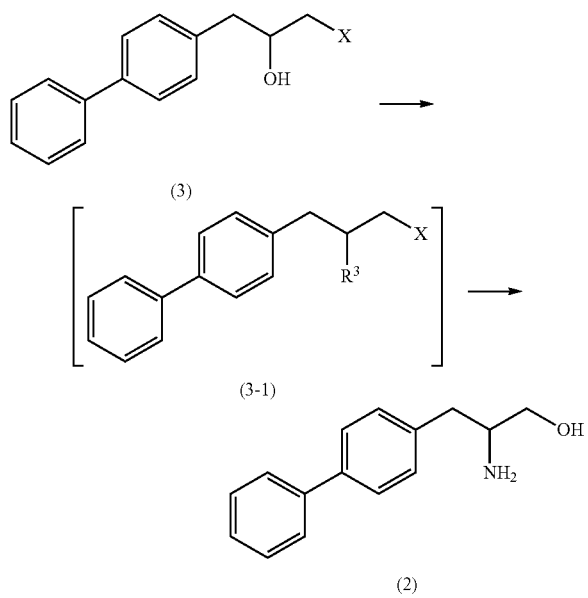

wherein X is halogen, preferably chloro, or —O—R5, wherein R5 is C$_1$-C$_6$-alkyl, preferably tert-butyl, and R3 is either an imide or an azide. In particular, the following examples describe the synthesis of (R)-3-([1,1-biphenyl]-4-yl)-2-aminopropan-1-ol hydrochloride

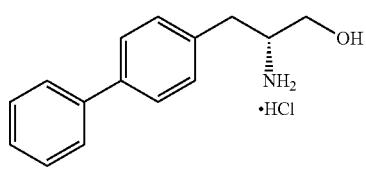 [SMILES: N[C@@H](CO)Cc1ccc(-c2ccccc2)cc1 ; Cl]

Example 2A-1

(R)-3-([1,1'-biphenyl]-4-yl)-2-aminopropan-1-ol hydrochloride via (R)-1-(1-([1,1'-biphenyl]-4-yl)-3-chloropropan-2-yl)pyrrolidine-2,5-dione (lab scale)

Step 1: (R)-1-(1-([1,1-biphenyl]-4-yl)-3-chloropropan-2-yl)pyrrolidine-2,5-dione

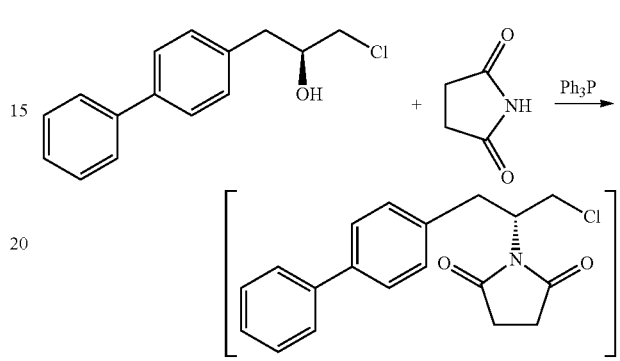

49.3 g (S)-1-([1,1'-biphenyl]-4-yl)-3-chloropropan-2-ol in 600 g toluene was added into a 1000 ml four-necked flask at about 70-80° C., and stirred until dissolved. The mixture was filtered and transferred to another reactor. Under nitrogen protection the solution was cooled down to about 0-5° C. and then 57.64 g triphenylphosphine and 20.79 g succinimide were added. After stirring the mixture, a solution of 40.02 g diethyl azodicarboxylate (DEAD) in 40 g toluene was added at about 0-5° C. Afterwards the toluene was removed under reduced pressure destillation. The title compound was recovered and directly used in the next step.

$[\alpha]_D^{25}$ +98.159 (c=0.01 g/ml, CHCl$_3$)

$^1$H-NMR (400 MHz, CDCl$_3$) δ 2.55-2.66 (m, 4H, CH$_2$), 3.17-3.30 (m, 2H, CH$_2$), 3.76 (dd, J=11.2, 4.8 Hz, 1H, CH$_2$), 4.23 (d, J=10.8 Hz, 1H, CH$_2$), 4.67-4.44 (m, 1H, CH), 7.26 (d, J=8.4 Hz, 2H, Ar—H), 7.34-7.38 (m, 1H, Ar—H), 7.43-7.47 (m, 2H, Ar—H), 7.54 (d, J=8.4 Hz, 2H, Ar—H), 7.58-7.60 (m, 2H, Ar—H)

Step 2: (R)-3-([1,1-biphenyl]-4-yl)-2-aminopropan-1-ol hydrochloride

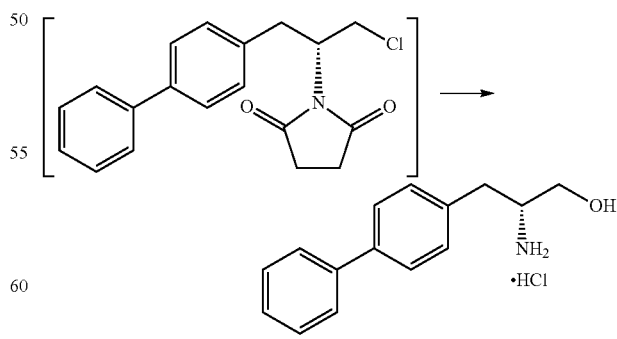

300 g water was added to the residue obtained in step 1. After heating the mixture to reflux and subsequent cooling down to 60-65° C., 102.8 g hydrochloric acid were added dropwise to the mixture. Then the mixture was heated to reflux, and the temperature maintained until the amount of the educt is 0.1% (checked by HPLC). Then the mixture was cooled down to about 80-90° C. After the addition of 433 g toluene, the mixture was heated to reflux, and then cooled to about 80-90° C. The phases were separated and the organic phase was recovered. The aqueous phase was adjusted to a pH of about 8-9 by addition of sodium hydroxide. Then, another 433 g toluene were added and the mixture heated to reflux, kept at reflux, and then cooled to about 75-80° C. The phases were separated again, the organic phase was recovered, and the aqueous layer was extracted with toluene. The mixture was again heated to reflux and kept at reflux, and after cooling the phases were separated, the organic phase was recovered, and the two organic phases extracted with toluene were combined. The combined phases were cooled down. Then a solution of hydrochloric acid in ethanol was added to the mixture and stirred. After cooling, the solids were filtered off, the filter cake was washed with toluene and dried at about 45-55° C. under vacuum to give 41.9 g of the title compound.

$[\alpha]_D^{25}$ +16.059 (c=0.01 g/ml, H$_2$O)

$^1$H-NMR (400 MHz, DMSO) δ 1.32 (s, 9H, CH$_3$), 2.60 (dd, J=13.6 8.4 Hz, 1H, CH$_2$), 2.86 (dd, J=13.6, 5.2 Hz, 1H, CH$_2$), 2.28-3.32 (m, 1H, CH$_2$), 3.35-3.39 (m, 1H, CH$_2$), 3.61-3.62 (m, 1H, CH), 4.72 (d, J=5.4 Hz, 1H, OH), 6.62 (d, J=8.6 Hz, 1H, NH), 7.28 (d, J=8.4 Hz, 2H, Ar—H), 7.30 (d, J=16.0 Hz, 1H, Ar—H), 7.45 (d, J=7.6 Hz, 2H, Ar—H), 7.56 (d, J=8.4 Hz, 2H, Ar—H), 7.63 (d, J=7.6 Hz, 2H, Ar—H).

The same reaction as under Example 2A-1, Step 1, was carried out by exchanging the solvent and adjusting the reaction temperature accordingly. The following overview summarizes the solvents used and the reaction conditions:

600 g toluene, 70-80° C., DEAD dissolved in 40 g toluene (see example above)

530 g ethyl acetate, 60-70° C., DEAD dissolved in 35 g of ethyl acetate 550 g tetrahydrofuran, 50-60° C., DEAD dissolved in 40 g of tetrahydrofuran 600 g dichloromethane, 30-35° C., DEAD dissolved in 50 g dichloromethane Example 2A-2

(R)-3-([1,1'-biphenyl]-4-yl)-2-aminopropan-1-ol hydrochloride via (R)-1-(1-([1,1'-biphenyl]-4-yl)-3-chloropropan-2-yl)pyrrolidine-2,5-dione (commercial scale)

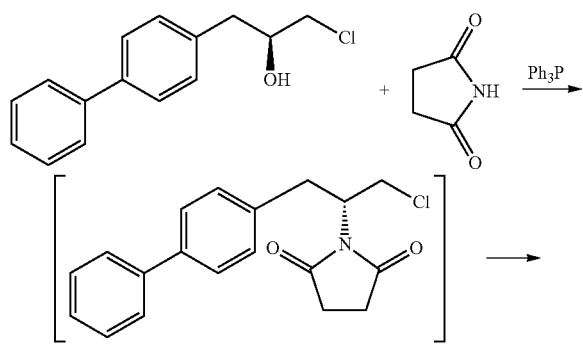

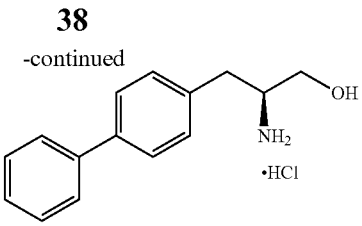

50 kg (S)-1-([1,1'-biphenyl]-4-yl)-3-chloropropan-2-ol was dissolved in 650 kg toluene at about 70-80° C. After about 1 h at this temperature the mixture was filtered, the filter rinsed with 20 kg toluene, and the solution transferred to another reactor. Under nitrogen protection the solution was cooled down to about 0-5° C. and 58.5 kg triphenylphosphine and 21 kg succinimide were added. After the mixture was stirred for 20 min, a solution of diethyl azodicarboxylate, previously prepared from 81.1 kg diethyl azodicarboxylate and 65 kg toluene, was added at about 0-5° C. for about 2-2.5 h. The temperature was maintained for about 3 h, then toluene was removed under vacuum at about 60-70° C. until no further toluene was distilled out. After the addition of 100 kg water, the mixture was refluxed until no further toluene was distilled out. Toluene and water were collected, separated and the water added back to the reactor. The reaction was cooled to about 70-80° C., then 103 kg 36% hydrochloric acid was added dropwise to the mixture. Then the mixture was heated at a speed of about 20-25° C./h to reflux. The temperature was maintained for about 15 h or until the amount of (R)-1-(1-([1,1'-biphenyl]-4-yl)-3-chloropropan-2-yl)pyrrolidine-2,5-dione was 0.2%. Then the mixture was cooled down to about 75-80° C. After the addition of 433 kg toluene, the mixture was heated to reflux, kept at reflux for about 30 min and then cooled to about 75-80° C. The phases were separated and the organic phase recovered. The aqueous phase was adjusted to a pH of about 8-9 by addition of 186.7 kg 30% sodium hydroxide solution. Then 433 kg toluene were added, the mixture heated to reflux, kept at reflux for about 30 min and then cooled to about 75-80° C. The phases were separated again and the aqueous layer was extracted with 216 kg toluene. The mixture was heated to reflux, kept at reflux for 30 min, then cooled to about 75-80° C. After separation of the phases the aqueous layer was adjusted to pH>10 by addition of about 27 kg 30% sodium hydroxide solution. After addition of 108 kg toluene at about 75-80° C., the mixture was heated to reflux, kept at reflux for another 30 min, and then cooled down to 75-80° C. The phases were separated, and the combined organic phases were cooled to about 55-65° C. Then 21.8 kg of a solution of 34% hydrochloric acid in ethanol was added over about 30 min. The mixture was stirred at about 55-65° C. for about 1 h, then cooled to about 25-35° C. After 1 h at 25-35° C., the solids were filtered off, the filter cake was washed with 44 kg toluene and dried at about 50-60° C. under vacuum to give 47.0 kg (R)-3-([1,1'-biphenyl]-4-yl)-2-aminopropan-1-ol hydrochloride (96-99% purity by HPLC, 98% ee).

Melting point: 264-272° C.

MS (ESI, m/e) 263.76

$[\alpha]_D^{25}$ +98.159 (c=0.01 g/ml, H$_2$O)

$^1$H-NMR (400 MHz, DMSO) δ 1.32 (s, 9H, CH$_3$), 2.60 (dd, J=13.6, 8.4 Hz, 1H, CH$_2$), 2.86 (dd, J=13.6, 5.2 Hz, 1H, CH$_2$), 2.28-3.32 (m, 1H, CH$_2$), 3.35-3.39 (m, 1H, CH$_2$), 3.61-3.62 (m, 1H, CH), 4.72 (d, J=5.4 Hz, 1H, OH), 6.62 (d, J=8.6 Hz, 1H, NH), 7.28 (d, J=8.4 Hz, 2H, Ar—H), 7.30 (d,

J=16.0 Hz, 1H, Ar—H), 7.45 (d, J=7.6 Hz, 2H, Ar—H), 7.56 (d, J=8.4 Hz, 2H, Ar—H), 7.63 (d, J=7.6 Hz, 2H, Ar—H).

Example 2B (R)-3-([1,1'-biphenyl]-4-yl)-2-aminopropan-1-ol hydrochloride via (R)-1-(1-([1:1'-biphenyl]-4-yl)-3-tert-butoxypropan-2-yl)pyrrolidine-2,5-dione (lab scale)

Step 1: (R)-1-(1-([1,1-biphenyl]-4-yl)-3-tert-butoxy-propan-2-yl)pyrrolidine-2,5-dione

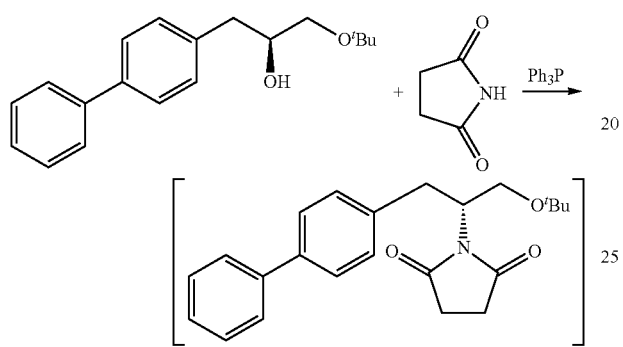

The reaction was carried out as described in Example 2A-1 using 50 g (S)-1-([1,1-biphenyl]-4-yl)-3-tert-butoxy-propan-2-ol as starting material, 50.91 g triphenylphosphine, 18.36 g succinimide, and 35.35 g DEAD in 40 g toluene. The title compound was recovered and directly used in the next step.

$[\alpha]_D^{25}$ +53.304 (c=0.01 g/ml, $H_2O$)

$^1$H-NMR (400 MHz, $CDCl_3$) δ 1.16 (s, 9H, $CH_3$), 2.45-2.58 (m, 4H, $CH_2$), 3.12 (dd, J=14.0, 6.0 Hz, 1H, $CH_2$), 3.27 (dd, J=14.0, 10.8 Hz, 1H, $CH_2$), 3.64 (dd, J=9.2, 5.6 Hz, 1H, $CH_2$), 3.88 (d, J=9.0 Hz, 1H, $CH_2$), 4.60-4.65 (m, 1H, CH), 7.26 (d, J=8.2 Hz, 2H, Ar—H), 7.35 (d, J=7.4 Hz, 1H, Ar—H), 7.44 (d, J=7.6 Hz, 2H, Ar—H), 7.51 (d, J=8.0 Hz, 2H, Ar—H), 7.59 (d, J=7.6 Hz, 2H, Ar—H).

Step 2: (R)-3-([1,1-biphenyl]-4-yl)-2-aminopropan-1-ol hydrochloride

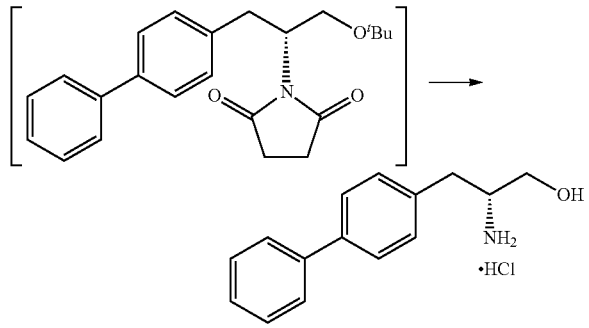

500 g water and 67.84 g sodium carbonate was added to the residue obtained in step 1. Then the mixture was heated to reflux, and the temperature maintained until the amount of the educt is ≤0.1% (checked by HPLC). Then the mixture was cooled down to about 80-90° C. After the addition of 433 g toluene, the mixture was heated to reflux, and then cooled to about 80-90° C. The phases were separated and the organic phase was recovered. The aqueous phase was adjusted to a pH of about 8-9 by addition of sodium hydroxide. Then, another 433 g toluene were added and the mixture heated to reflux and kept at reflux. The phases were separated again, the organic phase was recovered, and the aqueous layer was extracted with toluene. The mixture was again heated to reflux and kept at reflux. Then the phases were separated, the organic phase was recovered, and the two organic phases extracted with toluene were combined. The combined phases were cooled down. Then a solution of hydrochloric acid in ethanol was added to the mixture and stirred and cooled to 25-35° C. After cooling, the solids were filtered off, the filter cake was washed with toluene and dried at about 45-55° C. under vacuum to give 47.5 g of the title compound.

Example 2C (R)-3-([1,1'-biphenyl]-4-yl)-2-aminopropan-1-ol hydrochloride via (R)-3-([1,1'-biphenyl]-4-yl)-2-phthaloyl-chloropropane (lab scale)

Step 1: (R)-3-([1,1'-biphenyl]-4-yl)-2-phthaloyl-chloropropan

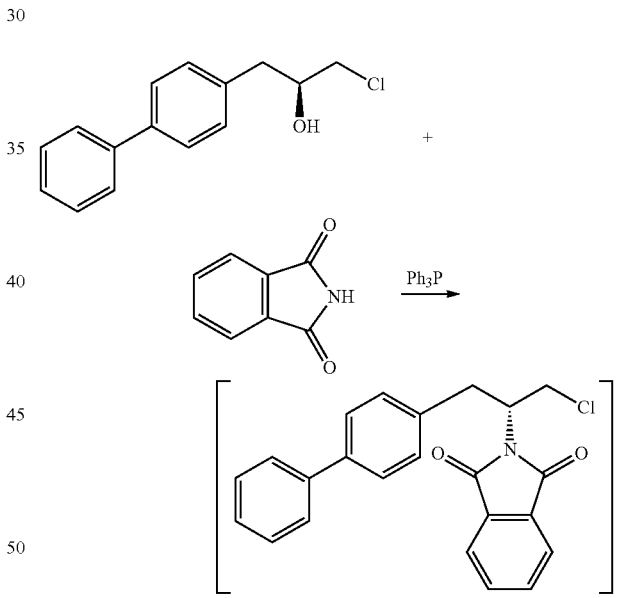

49.3 g (S)-1-([1,1'-biphenyl]-4-yl)-3-chloropropan-2-ol in 600 g toluene was added into a 1000 ml four-neck flask at about 70-80° C., and stirred until dissolved. The mixture was filtered, cooled down. Then 57.64 g triphenylphosphine and 30.66 g phthalimide were added. After stirring the mixture, a solution of 40.02 g diethyl azodicarboxylate (DEAD) in 40 g toluene was added at about 0-5° C. Afterwards the toluene was removed under reduced pressure distillation. The title compound was recovered and directly used in the next step.

$[\alpha]_D^{25}$ +176.95 (c=0.01 g/ml, $H_2O$)

$^1$H-NMR (400 MHz, $CDCl_3$) δ 3.17-3.32 (m, 2H, $CH_2$), 3.76 (dd, J=11.2, 4.8 Hz, 1H, $CH_2$), 4.15-4.20 (m, 1H, $CH_2$), 4.70-4.77 (m, 1H, CH), 7.17-7.19 (m, 2H, Ar—H), 7.21-7.25 (m, 1H, Ar—H), 7.25-7.34 (m, 2H, Ar—H), 7.39 (d,

J=8.0 Hz, 2H, Ar—H), 7.43-7.45 (m, 2H, Ar—H), 7.60-7.70 (m, 2H, Ar—H), 7.70-7.72 (m, 2H, Ar—H).

Step 2: (R)-3-([1,1-biphenyl]-4-yl)-2-aminopropan-1-ol hydrochloride

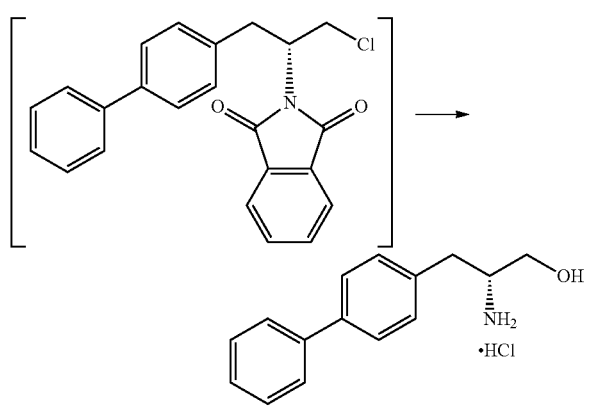

300 g water was added to the residue obtained in step 1. The mixture was heated to reflux, then cooled down to 60-65° C. Then 102.8 g hydrochloric acid was added dropwise to the mixture. Then the mixture was again heated to reflux, and the temperature maintained until the amount of the educt is ≤0.1% (checked by HPLC). Then the mixture was cooled down to about 80-90° C. After the addition of 433 g toluene, the mixture was heated to reflux, and then cooled to about 80-90° C. The phases were separated and the organic phase was recovered. The aqueous phase was adjusted to a pH of about 8-9 by addition of sodium hydroxide. Then, another 433 g toluene were added and the mixture heated to reflux and kept at reflux. The phases were separated again, the organic phase was recovered, and the aqueous layer was extracted with toluene. The mixture was again heated to reflux and kept at reflux. Then the phases were separated, the organic phase was recovered, and the two organic phases extracted with toluene were combined. The combined phases were cooled down. Then a solution of hydrochloric acid in ethanol was added to the mixture and stirred and cooled to 25-35° C. After cooling, the solids were filtered off, the filter cake was washed with toluene and dried at about 45-55° C. under vacuum to give 47.5 g of the title compound.

Example 2D (R)-3-([1,1'-biphenyl]-4-yl)-2-aminopropan-1-ol hydrochloride via (R)-3-([1,1'-biphenyl]-4-yl)-2-phthaloyl-tert-butoxypropane (lab scale)

Step 1: (R)-3-([1,1'-biphenyl]-4-yl)-2-phthaloyl-tert-butoxypropane

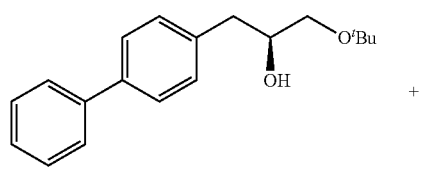

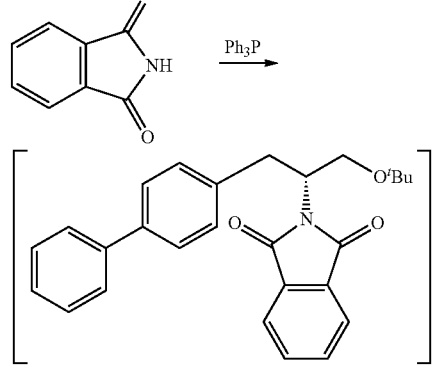

50 g (S)-1-([1,1'-biphenyl]-4-yl)-3-tert-butoxypropan-2-ol in 600 g toluene was added into a 1000 ml four-neck flask at about 70-80° C., and stirred until dissolved. The mixture was filtered, and cooled down. Then 50.91 g triphenylphosphine and 27.29 g phthalimide were added. After stirring the mixture, a solution of 35.35 g diethyl azodicarboxylate (DEAD) in 40 g toluene was added at about 0-5° C. Afterwards the toluene was removed under reduced pressure distillation. The title compound was recovered and directly used in the next step.

[α]D$^{25}$+53.304 (c=0.01 g/ml, CHCl$_3$)

$^1$H-NMR (400 MHz, CDCl$_3$) δ 1.19 (s, 9H), 2.75-3 (m, 2H), 3.54-3.79 (m, 2H), 4.27-4.33 (m, 1H), 7.35-7.40 (m, 5H), 7.51-7.52 (m, 4H), 7.84-7.90 (m, 4H).

Step 2: (R)-3-([1,1-biphenyl]-4-yl)-2-aminopropan-1-ol hydrochloride

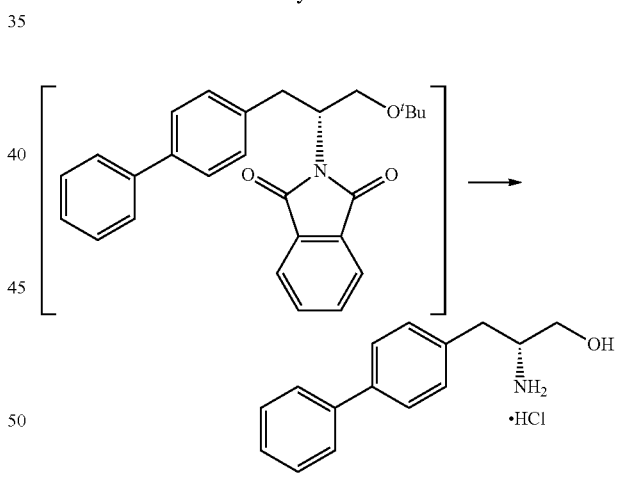

500 g water and 67.84 g sodium carbonate were added to the residue obtained in step 1. The mixture was heated to reflux, and the temperature maintained until the amount of the educt is ≤0.1% (checked by HPLC). Then the mixture was cooled down to about 80-90° C. The following reaction steps are carried out exactly as described under step 2 of Example 2C. After drying at about 45-55° C. under vacuum 45.5 g of the title compound were obtained.

Example 3-A

The following examples describe the synthesis of compounds falling under general formula (1) according to the following general reaction

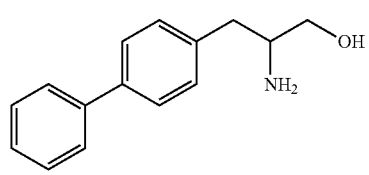

(2)

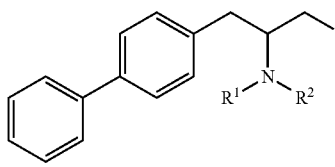

(1)

wherein R1 and R2 are independently of each other, hydrogen or a nitrogen protecting group, as defined herein below, wherein at least one of R1 or R2 is a nitrogen protecting group.

Example 3A (R)-tert-butyl (1-([1,1'-biphenyl]-4-yl)-3-hydroxypropan-2-yl)carbamate (labscale)

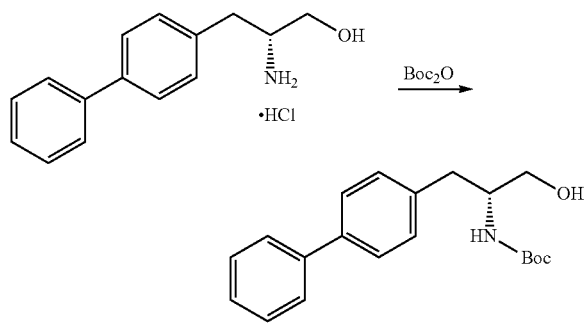

52.7 g (R)-3-([1,1'-biphenyl]-4-yl)-2-aminopropan-1-ol hydrochloride, 231 g water and 168 g ethanol were added into a 1000 ml four-neck flask and stirred until dissolved. Then, sodium hydroxide was added, and the mixture heated to about 55-60° C. Then 48.4 g di-tert-butyl dicarbonate was added and the temperature maintained for 1.5 h. Finally, 75 g water were added and then the mixture was concentrated under vacuum distillation at an inner temperature of 45-50° C. until all ethanol is removed. Then the mixture was cooled, and the precipitate filtered and the filter cake washed with water and dried in an air oven at about 65-70° C. to give 62.7 g of the title compound.

$[\alpha]_D^{25}$ +21.780 (c=0.01 g/ml, CHCl$_3$)

$^1$H-NMR (400 MHz, DMSO) δ 1.32 (s, 9H, CH$_3$), 2.60 (dd, J=13.6, 8.4 Hz, 1H, CH$_2$), 2.86 (dd, J=13.6, 5.2 Hz, 1H, CH$_2$), 2.28-3.32 (m, 1H, CH$_2$), 3.35-3.39 (m, 1H, CH$_2$), 3.61-3.62 (m, 1H, CH), 4.72 (d, J=5.4 Hz, 1H, OH), 6.62 (d, J=8.6 Hz, 1H, NH), 7.28 (d, J=8.4 Hz, 2H, Ar—H), 7.30 (d, J=16.0 Hz, 1H, Ar—H), 7.45 (d, J=7.6 Hz, 2H, Ar—H), 7.56 (d, J=8.4 Hz, 2H, Ar—H), 7.63 (d, J=7.6 Hz, 2H, Ar—H).

Example 3B (R)-tert-butyl (1-([1,1'-biphenyl]-4-yl)-3-hydroxypropan-2-yl)carbamate (1-a)* (industrial scale)

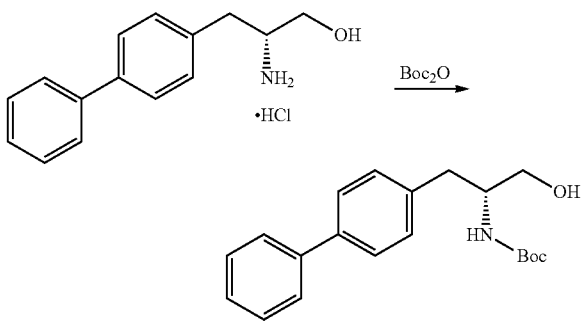

(1-a)*

A mixture of 50 kg (R)-3-([1,1'-biphenyl]-4-yl)-2-aminopropan-1-ol hydrochloride, 120 kg ethanol and 50 kg water is stirred for 20 min. Then a solution of 27.8 kg 30% sodium hydroxide solution is added at about 20-25° C. The mixture is heated to about 55-60° C. and 45.5 kg di-tert-butyl dicarbonate is added slowly. After the mixture is stirred for another 1 h, 75 kg water are added and the mixture is then concentrated under vacuum distillation at an inner temperature of 50° C. until ethanol is removed. After the mixture is cooled to about 25-30° C. the precipitate is filtered and the filter cake is washed with 50 kg water and dried in an air oven at about 70-75° C. to give 59.6 kg (R)-tert-butyl (1-([1,1'-biphenyl]-4-yl)-3-hydroxypropan-2-yl)carbamate (97-99% purity by HPLC, >99% ee) Melting point: 114-116° C.

MS (ESI, m/e) 327.42

$[\alpha]_D^{25}$ +21.780 (c=0.01 g/ml, CHCl$_3$)

$^1$H-NMR (400 MHz, DMSO) δ 1.32 (s, 9H, CH$_3$), 2.60 (dd, J=13.6, 8.4 Hz, 1H, CH$_2$), 2.86 (dd, J=13.6, 5.2 Hz, 1H, CH$_2$), 2.28-3.32 (m, 1H, CH$_2$), 3.35-3.39 (m, 1H, CH$_2$), 3.61-3.62 (m, 1H, CH), 4.72 (d, J=5.4 Hz, 1H, OH), 6.62 (d, J=8.6 Hz, 1H, NH), 7.28 (d, J=8.4 Hz, 2H, Ar—H), 7.30 (d, J=16.0 Hz, 1H, Ar—H), 7.45 (d, J=7.6 Hz, 2H, Ar—H), 7.56 (d, J=8.4 Hz, 2H, Ar—H), 7.63 (d, J=7.6 Hz, 2H, Ar—H).

Example 4-A (R)-5-biphenyl-4-yl-4-tert-butoxycarbonylamino-2-methylpent-2-enoic acid (lab scale)

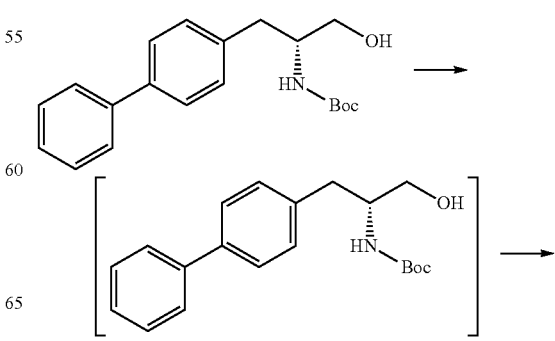

-continued

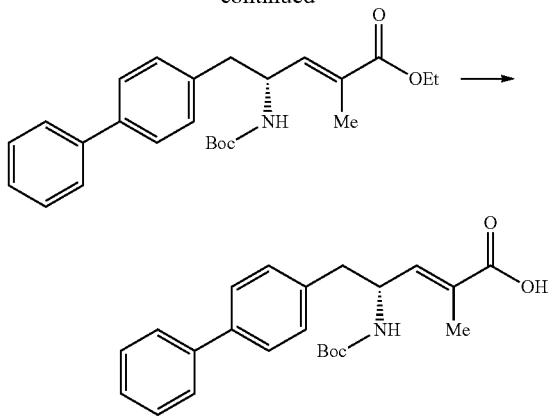

240 g water, 700 g isopropyl acetate, 23.6 g NaBr, 15.6 g NaHCO₃ and 40 g (R)-tert-butyl-(1-([1,1-biphenyl]-4-yl)-3-hydroxypropan-2-yl)carbamate were added into a 2 L four-necked flask and the mixture was stirred until dissolved. The mixture was cooled to 0-5° C. Then, 0.39 g TEMPO reagent was added and 105 g NaClO (12% w/w active chlorine content) solution were added in a dropwise manner while the temperature was held at 0-5° C. The mixture was stirred at that temperature until all starting material was used up (control by TLC). Then an aqueous solution of sodium thiosulfate was added while warming the temperature to 20-25° C. The mixture was stirred, and the phases separated. The organic phase was recovered. While keeping the temperature at 20-25° C., 51.3 g of the phosphorous ylide carbethoxyethylidene-triphenylphosphorane were added and the reaction mixture was stirred until the reaction was complete (control by TLC). Then the isopropyl acetate was fully removed via distillation under reduced pressure in a water bath with a temperature of 60-70° C. Then 150 g industrial ethanol was added and the mixture again subjected to reduced pressure distillation to remove all solvent. Then 212.5 g water, 385 g industrial ethanol and 9 g lithium hydroxide were added to the residue. The mixture was heated to reflux. When there was no raw material left (control by TLC), the mixture was cooled to about 70° C. Then a solution of dilute acetic acid obtained by mixing 45 g acetic acid and 165 g water was slowly added. The mixture was then again heated to reflux. After the mixture was cooled to about 8-12° C., the precipitate was filtered, and the filter cake washed with water and dried at 65-70° C. to give the title compound (44.6 g, yield 91.1%).

Melting point: 197° C.
MS (ESI, m/e) 381.0
¹H-NMR (600 MHz, DMSO) δ 1.33 (s, 9H, CH₃), 1.61 (s, 3H, CH₃), 2.71 (m, 1H, CH₂), 2.88 (m, 1H, CH₂), 4.84 (m, 1H, CH), 6.55 (d, 1H, CH=C), 7.16 (m, 1H, N—H), 7.29 (m, 2H, Ar—H), 7.33 (m, 1H, Ar—H), 7.44 (m, 2H, Ar—H), 7.56 (m, 2H, Ar—H), 7.62 (m, 2H, Ar—H), 12.30 (s, 1H, CO₂H).

Example 4-B (R)-5-biphenyl-4-yl-4-tert-butoxycarbonylamino-2-methylpent-2-enoic acid (commercial scale)

480 kg water, 1400 kg isopropyl acetate, 47.2 kg NaBr, 31.2 kg NaHCO₃ and 80 kg (R)-tert-butyl-(1-([1,1-biphenyl]-4-yl)-3-hydroxypropan-2-yl)carbamate were added into a 3000 L reactor and the mixture was stirred for 30 min. The mixture was cooled to 0-5° C. Then, 0.78 kg TEMPO reagent was added and 210 kg NaClO (12% w/w active chlorine content) solution were added over a period of 30 min while the temperature was held at 0-5° C. The mixture was stirred at that temperature for 30-45 min. Then an aqueous solution of 24 kg sodium thiosulfate in 200 kg water was added. The reaction mixture was warmed to a temperature of 20-25° C. and stirred for 15 min. Then the phases were separated. The organic phase was recovered. While keeping the temperature at 20-25° C., 102.6 kg of the phosphorous ylide carbethoxyethylidene-triphenylphosphorane were slowly added and the reaction mixture was stirred 1.5 h. Then around 1300 kg isopropyl acetate were removed via distillation under reduced pressure at a temperature of 60-70° C. Then 300 kg ethanol was added and the mixture again subjected to reduced pressure distillation to remove the solvent. Then 425 kg water, 770 kg ethanol and 18 kg lithium hydroxide were added to the residue. The mixture was heated to reflux for 1 h. Then the mixture was cooled to about 70° C., and a solution of dilute acetic acid (90 kg acetic acid in 330 kg water) was added. The mixture was then again heated to reflux for 0.5 h. Afterwards the mixture is cooled to about 8-12° C. and stirred for another 0.5 h. The precipitate is filtered, and the filter cake washed with a mixture of 90 kg ethanol and 115 kg water at 8-12° C. Drying of the filter cake affords the crude title compound (80 kg, yield 81.7%).

A 2000 L reactor was charged with 540 kg ethanol and 80 kg of the crude title compound; then 4 kg activated charcoal were added and the mixture was heated to reflux for 30 min. Afterwards the mixture was filtered into another 2000 L reactor, and the charcoal was washed with 100 kg of hot ethanol. The combined filtrate was mixed with 640 kg of purified water and heated to reflux for 30 min, then the mixture was slowly cooled to 8-12° C. and stirred for another hour. The precipitate was filtered and the filter cake washed with a mixture of 64 kg ethanol and 64 kg purified water at 8-12° C. The filter cake was dried at 65-70° C. to yield the title compound (yield 70.2-74.9%, purity>99.5%).

The invention claimed is:
1. A process for preparing a compound of formula (2), or a salt thereof,

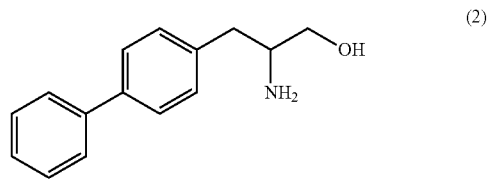 [SMILES: NC(CO)Cc1ccc(-c2ccccc2)cc1]

comprising the steps of
(a) reacting a compound of formula (3), or salt thereof

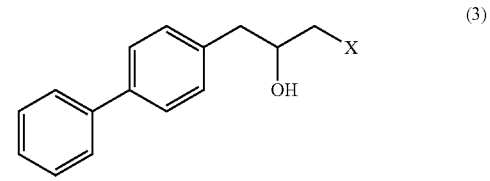

wherein X is halogen or —O—R5, wherein R5 is C₁-C₆-alkyl with an imide or azide nitrogen nucleophile under Mitsunobu conditions;
(b) (i) conversion of the resulting imide intermediate compound of formula (3-1) or salt thereof,

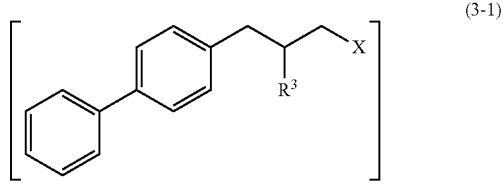
(3-1)

wherein X is halogen or —O—R5, wherein R5 is $C_1$-$C_6$-alkyl and R3 is an imide,
by hydrolysis or by treatment with hydrazine to obtain a compound of formula (2) or salt thereof,
or
(ii) reduction of the resulting intermediate azide compound of formula (3-1) or salt thereof,

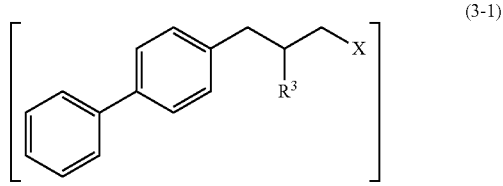
(3-1)

wherein X is halogen or —O—R5, wherein R5 is $C_1$-$C_6$-alkyl and R3 is azide,
to obtain a compound of formula (2) or salt thereof.

2. A process according to claim 1, wherein the reaction with the imide or azide nitrogen nucleophile under Mitsunobu conditions is carried out in the presence of a phosphorous(III) compound, and a dialkyl azodicarboxylate.

3. A process according to claim 1, wherein the imide nitrogen nucleophile is selected from the group consisting of succinimide, phthalimide, substituted succinimide, substituted phthalimide, naphthalimide, substituted naphthalimide, maleinimide and substituted maleinimide.

4. A process according to claim 1, wherein the compound of formula (3), or salt thereof

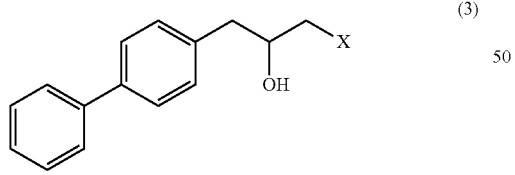
(3)

is of formula (3-a) or salt thereof

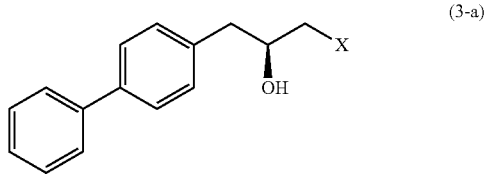
(3-a)

wherein X is halogen or —O—R5, wherein R5 is $C_1$-$C_6$-alky;
and is prepared
by reacting a compound of formula (4-a),

(4-a)

wherein X is halogen or —O—R5, wherein R5 is $C_1$-$C_6$-alkyl;
with a biphenylic compound, to obtain a compound of formula (3-a) or salt thereof.

5. A process according to claim 1, wherein the compound of formula (2) is of formula (2-a) or salt thereof

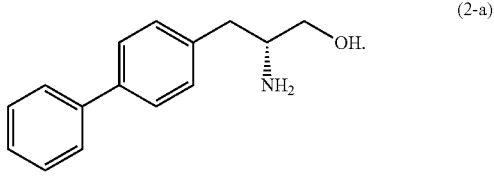 [SMILES: N[C@@H](CO)Cc1ccc(-c2ccccc2)cc1]
(2-a)

6. A process according to claim 1, wherein the compound of formula (3) is of formula (3-a) or salt thereof

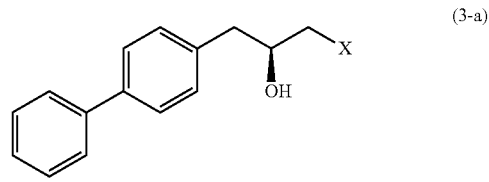
(3-a)

wherein X is halogen or —O—R5, wherein R5 is $C_1$-$C_6$-alkyl.

7. A process according to claim 1, wherein the compound of formula (3-1) is of formula (3-1-a) or salt thereof,

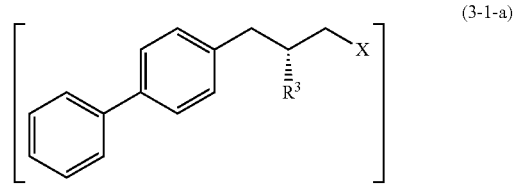
(3-1-a)

wherein X is halogen or —O—R5, wherein R5 is $C_1$-$C_6$-alkyl and R3 is imide.

8. A process according to claim 7, wherein R3 is an azide.

9. A process according to claim 2, wherein the phosphorous (III) compound is a phosphine or ylide.

10. A process according to claim 9, wherein the phosphorous (III) compound is more preferably triphenylphosphine or tri-n-butylphosphine, and the dialkyl azodicarboxylate is diethyl azodicarboxylate (DEAD) or diisopropyl azodicarboxylate (DIAD).

11. A process according to claim 3, wherein the imide nitrogen nucleophile is selected from succinimide and phthalimide.

12. A process according to claim 4, wherein the compound of formula (3) is of formula (3-a) or salt thereof

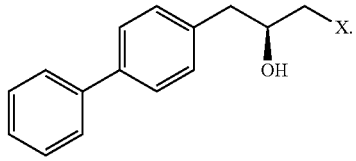 (3-a)

13. A process according to claim 4, wherein said activated biphenylic compound is selected from the group consisting of biphenylmagnesium halide, di(biphenyl)magnesium, biphenyllithium, biphenylcuprate (low and higher-order cuprates) and biphenylzinc.

14. A process according to claim 4, wherein said activated biphenylic compound is biphenylmagnesium halide.

15. A process according to claim 4, wherein the reaction is carried out in the presence of cuprate (I) ions.

16. A process for preparing a compound of formula (1), or a salt thereof,

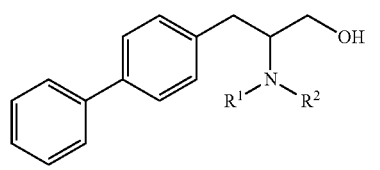 (1)

wherein R1 and R2 are, independently of each other, hydrogen or a nitrogen protecting group,
wherein at least one of R1 or R2 is a nitrogen protecting group,
comprising converting a compound of formula (2), or a salt thereof,

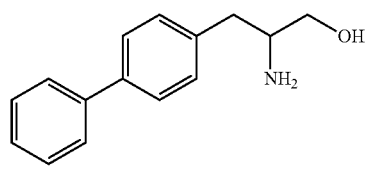 (2)

into a compound of formula (1), or a salt thereof, by introduction of a nitrogen protecting group.

17. A process according to claim 16, wherein the hydrochloride salt of the compound of formula (2-a)

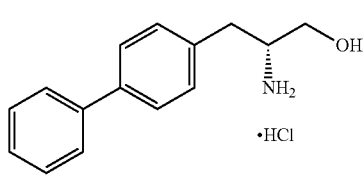 (2-a)

is obtained from a compound of formula (3-1-a)

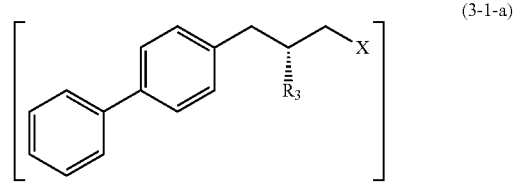 (3-1-a)

wherein X is chloro or tert-butoxy, and R3 is succinimidyl or phthalimidyl,
by hydrolysis with an inorganic acid or an inorganic base, and optionally subsequent treatment with hydrochloric acid.

18. A process according to claim 17, wherein the compound of formula (3-1-a)

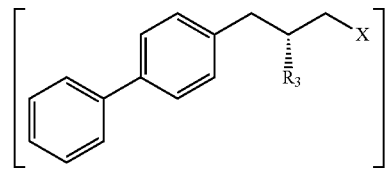 (3-1-a)

wherein X is chloro or tert-butoxy, and R3 is succinimidyl or phthalimidyl,
is obtained from a compound of formula (3-a)

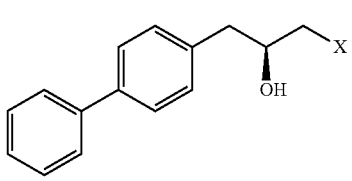 (3-a)

wherein X is chloro or tert-butoxy;
by reaction under Mitsunobu conditions with an imide selected from succinimide and phthalimide in the presence of triphenyl phosphine and a dialkyl azodicarboxylate compound in an organic solvent.

19. A process according to claim 18, wherein the dialkyl azodicarboxylate compound is diethyl azodicarboxylate (DEAD), and the organic solvent is selected from toluene, ethyl acetate, tetrahydrofurane, and dichloromethane.

20. A process according to claim 18, wherein said compound of formula (3-a)

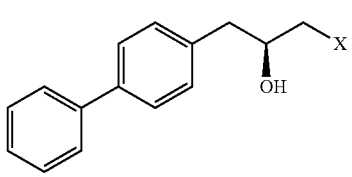 (3-a)

wherein X is chloro or tert-butoxy;
is obtained by a Grignard reaction comprising reacting 4-bromobiphenyl and metallic magnesium in tetrahydrofuran and then reacting the obtained 4-biphenyl-magnesium bromide with a compound of formula (4-a)

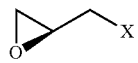
(4-a)

wherein X is chloro or tert-butoxy, in the presence of a cuprous (I) halide, preferably cuprous iodide.

21. A process according to claim 16, wherein the nitrogen protecting group is tert-butoxy-carbonyl.

22. A process according to claim 16, wherein the obtained compound of formula (1) or salt thereof

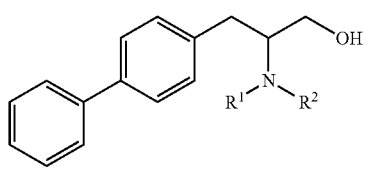
(1)

wherein R1 and R2 are, independently of each other, hydrogen or a nitrogen protecting group, wherein at least one of R1 or R2 is a nitrogen protecting group, is subjected to a TEMPO mediated oxidation reaction to obtain a compound of formula (5) or salt thereof,

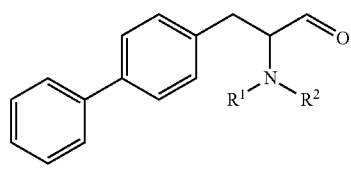
(5)

wherein R1 and R2 are, independently of each other, hydrogen or a nitrogen protecting group and at least one of R1 or R2 is a nitrogen protecting group.

23. A process according to claim 16, wherein X is halogen or —O—R5, wherein R5 is $C_1$-$C_6$-alkyl.

24. A process according to claim 16, wherein the compound of formula (1) is of formula (1-a)

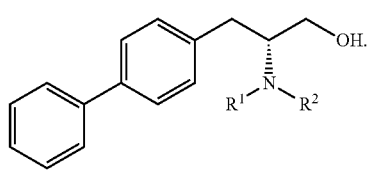
(1-a)

25. A process according to claim 16, where wherein the compound of formula (2) is of formula (2-a) or salt thereof

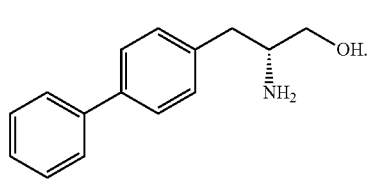
(2-a)

26. A process according to claim 24, wherein the compound of formula (1-a) is (R)-tert-butyl (1-([1,1'-biphenyl]-4-yl)-3-hydroxypropan-2-yl)carbamate of the following formula (1-a)*:

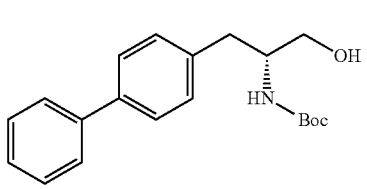
(1-a)* which is obtained by reacting the hydrochloride salt of the compound of formula (2-a) with di-tert-butyl dicarbonate.

27. A process according to claim 22, wherein the compound of formula (1) of the formula (1-a) or salt thereof,

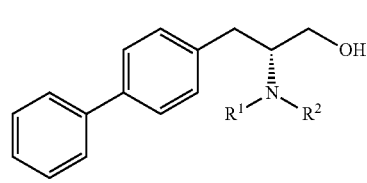
(1-a)

wherein R1 and R2 are, independently of each other, hydrogen or a nitrogen protecting group, and wherein at least one of R1 or R2 is a nitrogen protecting group.

28. A process according to claim 22, wherein the compound of formula (1-a) is the compound (R)-tert-butyl (1-([1,1'-biphenyl]-4-yl)-3-hydroxypropan-2-yl)carbamate of formula (1-a)*

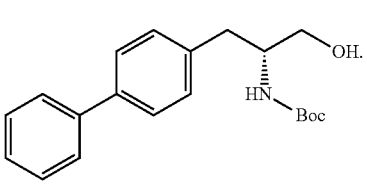
(1-a)*

29. A process according to claim 22, wherein the compound of formula (5) is a compound of formula (5-a)

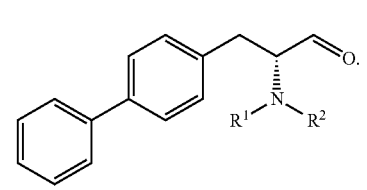
(5-a)

30. A process according to claim 22, wherein the compound of formula (5-a) is a compound of formula (5-a)*

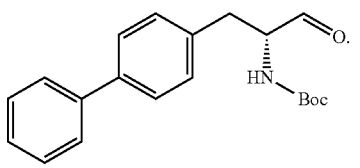
(5-a)*

31. A process for preparing a compound of formula (1), or a salt thereof,

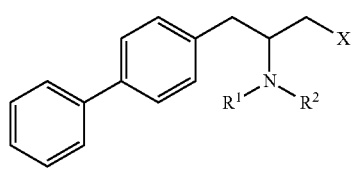
(1)

wherein R1 and R2 are, independently of each other, hydrogen or a nitrogen protecting group,
wherein at least one of R1 or R2 is a nitrogen protecting group,
comprising the steps
a) reacting a compound of formula (4),

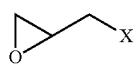
(4)

wherein X is halogen or —O—R5, wherein R5 is $C_1$-$C_6$-alkyl;
with a biphenylic compound;
b) reacting the resulting compound of formula (3), or salt thereof

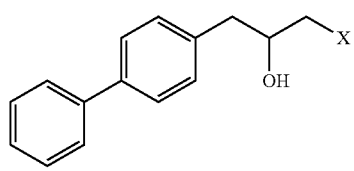
(3)

wherein X is halogen or —O—R5, wherein R5 is $C_1$-$C_6$-alkyl;
with an imide or azide nitrogen nucleophile under Mitsunobu conditions;
c) (i) converting the resulting imide intermediate compound of formula (3-1) or salt thereof,

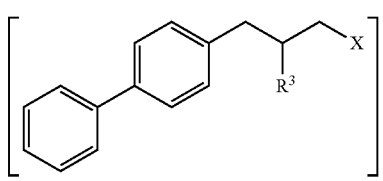
(3-1)

wherein X is halogen or —O—R5, wherein R5 is $C_1$-$C_6$-alkyl, and R3 is an imide,
by hydrolysis or by treatment with hydrazine to obtain a compound of formula (2) or salt thereof, preferably of formula (2-a) or salt thereof, or
(ii) reducing the resulting intermediate azide compound of formula (3-1) or salt thereof,

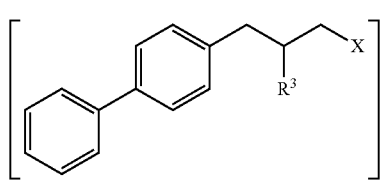
(3-1)

wherein X is halogen or —O—R5, wherein R5 is $C_1$-$C_6$-alkyl, and R3 is azide,
to obtain a compound of formula (2) or salt thereof;
d) converting the resulting compound of formula (2), or a salt thereof,

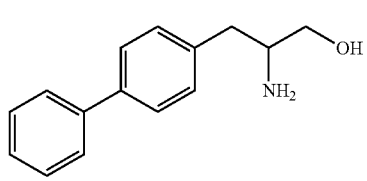
(2)

into a compound of formula (1), or a salt thereof by introduction of a nitrogen protecting group.

32. A process according to claim 31, wherein the compound of formula (1) is of formula (1-a)

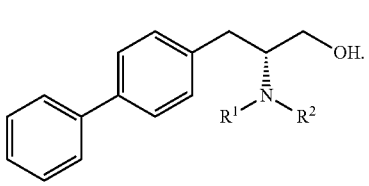
(1-a)

33. A process according to claim 31, wherein the compound of formula (4) is of formula (4-a)

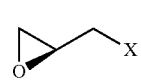
(4-a)

wherein X is halogen or —O—R5, wherein R5 is $C_1$-$C_6$-alkyl.

34. A process according to claim 31, wherein the compound of formula (3) is of formula (3-a) or salt thereof

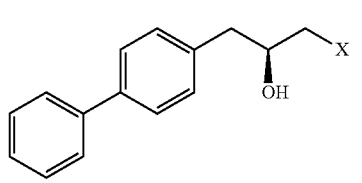
(3-a)

wherein X is halogen or —O—R5, wherein R5 is $C_1$-$C_6$-alkyl.

35. A process according to claim 31, wherein the compound of formula (3-1) is of formula (3-1-a) or salt thereof,

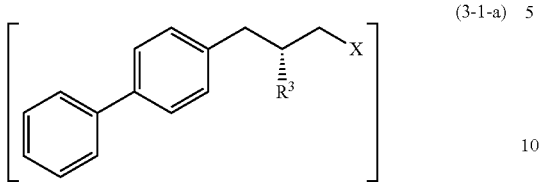

(3-1-a)

wherein X is halogen or —O—R5, wherein R5 is $C_1$-$C_6$-alkyl, and R3 is imide.

36. A process according to claim 31, wherein the compound of formula (3-1) is of formula (3-1-a) or salt thereof,

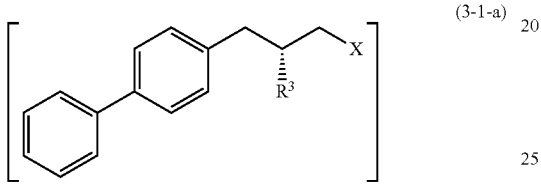

(3-1-a)

wherein X is halogen or —O—R5, wherein R5 is $C_1$-$C_6$-alkyl, and R3 is azide.

37. A process according to claim 31, wherein the compound of formula (2) is of formula (2-a) or salt thereof

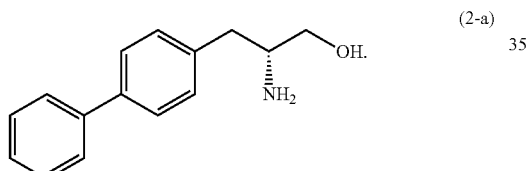

(2-a)

38. A compound of formula (3-1-a) or salt thereof in substantially optically pure form

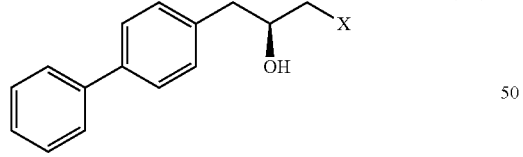

(3-a)

wherein R3 is imide or azide.

39. A process for preparing a compound of formula (5), or a salt thereof,

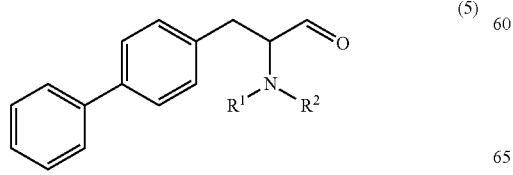

(5)

wherein R1 and R2 are, independently of each other, hydrogen or a nitrogen protecting group and at least one of R1 or R2 is a nitrogen protecting group, by oxidizing a compound of formula (1) or salt thereof

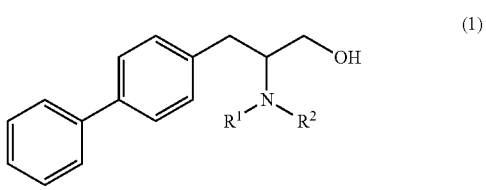

(1)

wherein R1 and R2 are, independently of each other, hydrogen or a nitrogen protecting group, wherein at least one of R1 or R2 is a nitrogen protecting group, in a TEMPO mediated oxidation reaction to obtain a compound of formula (5) or salt thereof of formula (5-a) or salt thereof.

40. A process according to claim 39, wherein the compound of formula (5) is of formula (5-a)

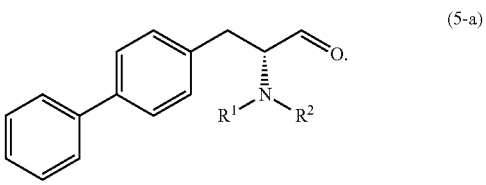

(5-a)

41. A process according to claim 40, wherein the compound of formula (5-a) is of formula (5-a)*

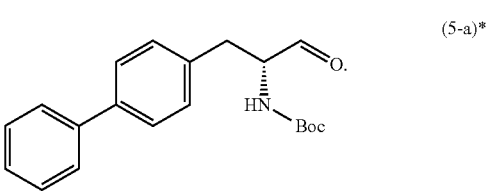 [SMILES: CC(C)(C)OC(=O)N[C@@H](C=O)Cc1ccc(-c2ccccc2)cc1]

(5-a)*

42. A process according to claim 39, wherein the compound of formula (1) is of formula (1-a) or a salt thereof,

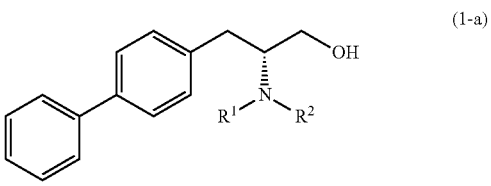

(1-a)

wherein R1 and R2 are, independently of each other, hydrogen or a nitrogen protecting group, and wherein at least one of R1 or R2 is a nitrogen protecting group.

43. A process according to claim 39, wherein the compound of formula (1-a) is an (R)-tert-butyl (1-([1,1'-biphe nyl]-4-yl)-3-hydroxypropan-2-yl)carbamate of formula (1-a)*

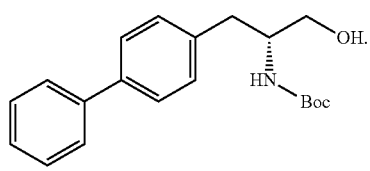

(1-a)*

44. A process for preparing N-(3-carboxyl-1-oxopropyl)-(4S)-(p-phenylphenylmethyl)-4-amino-(2R)-methyl butanoic acid ethyl ester, or a salt thereof, comprising
  i. the manufacture of a compound of formula (3-a) or salt thereof in substantially optically pure form

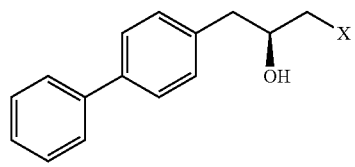

(3-a)

wherein X is halogen or —O—R5, wherein R5 is $C_1$-$C_6$-alkyl, or
  ii. the manufacture of a compound of formula (3-1-a) or salt thereof as defined in claim 38, or iii. the manufacture of a compound of formula (2-a) or salt thereof in substantially optically pure form

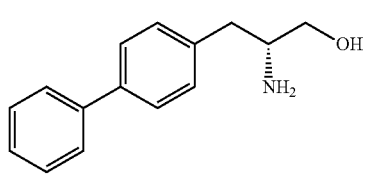

(2-a)

or
  iv. the manufacture of a compound of formula (1-a)

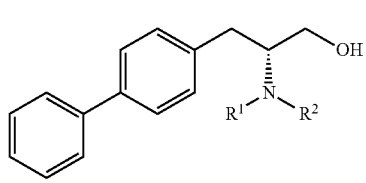

(1-a)

wherein R1 and R2 are, independently of each other, hydrogen or a nitrogen protecting group, wherein at least one of R1 or R2 is a nitrogen protecting group, or salt thereof.

* * * * *